US006447545B1

(12) United States Patent
Bagby

(10) Patent No.: US 6,447,545 B1
(45) Date of Patent: Sep. 10, 2002

(54) SELF-ALIGNING BONE IMPLANT

(76) Inventor: George W. Bagby, 105 W. 8th Ave. Ste. 438, Spokane, WA (US) 99204-2318

(*) Notice: Subject to any disclaimer, the term of this patent is extended or adjusted under 35 U.S.C. 154(b) by 0 days.

(21) Appl. No.: 09/609,129

(22) Filed: Jul. 1, 2000

(51) Int. Cl.[7] .................................................. A61F 2/44
(52) U.S. Cl. ............................. 623/17.16; 623/17.11; 623/16.11; 606/61
(58) Field of Search ..................... 623/16.11–23.63; 606/61, 60, 62–68, 72, 86, 53

(56) References Cited

U.S. PATENT DOCUMENTS

| 4,501,269 A | 2/1985 | Bagby | 128/92 |
| 4,662,891 A | 5/1987 | Noiles | 623/22 |
| 4,778,469 A | 10/1988 | Lin et al. | 623/16 |
| 4,828,563 A | 5/1989 | Muller-Lierheim | 623/16 |
| 4,834,757 A | 5/1989 | Brantigan | 623/17 |
| 4,878,915 A | 11/1989 | Brantigan | 623/17 |
| 4,898,161 A | 2/1990 | Grundei | 606/105 |
| 4,946,378 A | 8/1990 | Hirayama et al. | 623/17 |
| 4,961,740 A | 10/1990 | Ray et al. | 606/61 |
| 5,015,247 A | 5/1991 | Michelson | 606/61 |
| 5,055,104 A | 10/1991 | Ray | 606/61 |
| 5,074,880 A | 12/1991 | Mansat | 623/20 |
| 5,084,050 A | 1/1992 | Draenert | 606/77 |
| 5,171,327 A | 12/1992 | Koch et al. | 623/16 |
| 5,263,953 A | 11/1993 | Bagby | 606/61 |
| 5,403,136 A | 4/1995 | Mathys | 411/310 |
| 5,423,817 A | 6/1995 | Chih-I LIn | 606/61 |
| 5,443,515 A | 8/1995 | Cohen et al. | 623/17 |
| 5,458,638 A * | 10/1995 | Kuslich et al. | 606/61 |
| 5,489,307 A | 2/1996 | Kuslich et al. | 623/17 |
| 5,489,308 A | 2/1996 | Kuslich et al. | 623/17 |
| 5,534,029 A | 7/1996 | Shima | 623/17 |
| 5,534,031 A | 7/1996 | Matsuzaki et al. | 623/17 |
| 5,591,235 A | 1/1997 | Kuslich | 623/17 |
| 5,645,598 A | 7/1997 | Brosnahan, III | 623/17 |
| 5,665,122 A | 9/1997 | Kambin | 623/17 |
| 5,702,455 A | 12/1997 | Saggar | 623/17 |
| 5,709,683 A | 1/1998 | Bagby | 606/61 |
| 5,720,748 A | 2/1998 | Kuslich et al. | 606/80 |
| 5,743,912 A * | 4/1998 | Lahille et al. | 606/65 |
| 5,904,719 A | 5/1999 | Errico et al. | 623/17 |
| 5,906,616 A | 5/1999 | Pavlov et al. | 606/61 |
| 5,968,098 A | 10/1999 | Winslow | 623/17 |
| 6,010,502 A | 1/2000 | Bagby | 623/61 |
| 6,015,436 A | 1/2000 | Schönhöffer | 623/17 |
| 6,120,502 A * | 9/2000 | Michelson | 606/61 |
| 6,210,412 B1 * | 4/2001 | Michelson | 606/61 |

FOREIGN PATENT DOCUMENTS

DE 3505567 A1 6/1986

OTHER PUBLICATIONS

"Stress Shielding Reduced by a Silicon Plate–Bone Interface", Donna L. Korvick, Jarrett W. Newbrey, George W. Bagby, Ghery D. Pettit & James D. Lincoln, Acta Orthop Scand; 1989, 60(5):611–6, pp. 611–616.

"Transmission of Disease Through Transplantation of Musculoskeletal Allografts", The Journal of Bone and Joint Surgery, Nov., 1995, 77–A, pp. 1742–1754.

"Anterior Cervical Interbody Fusion With Threaded Cylindrical Bone", Jose M. Otero Vich, M.D.; J. Neurosurg., vol. 63, Nov., 1985, pp. 750–753.

* cited by examiner

Primary Examiner—David J. Isabella
Assistant Examiner—Urmi Chattopadhyay
(74) Attorney, Agent, or Firm—Wells St. John P.S.

(57) ABSTRACT

A bone joining implant includes a tubular body. The tubular body has an axially extending outer surface defining an outer dimension of substantially uniform cross-section and including a smooth leading insertion portion and a bone engaging trailing portion.

43 Claims, 15 Drawing Sheets

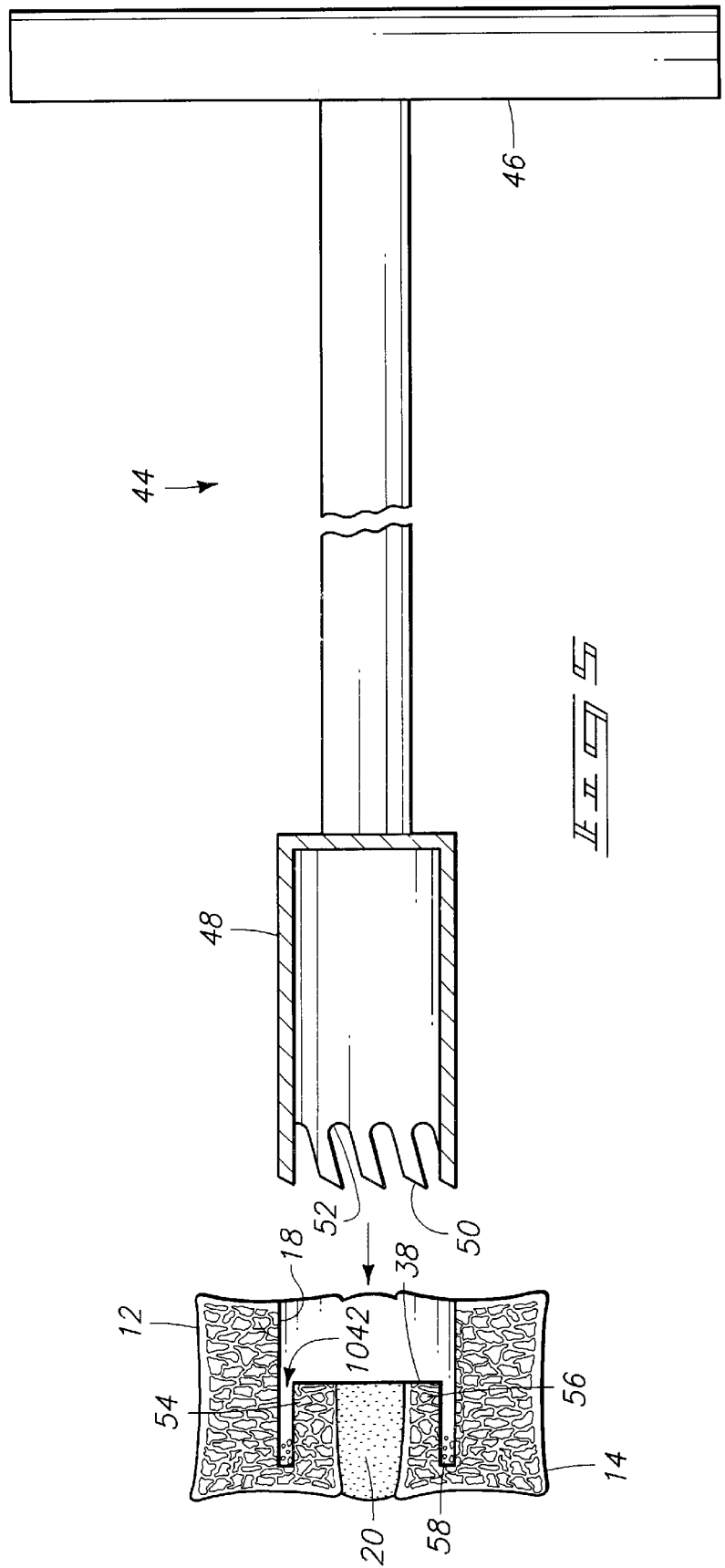

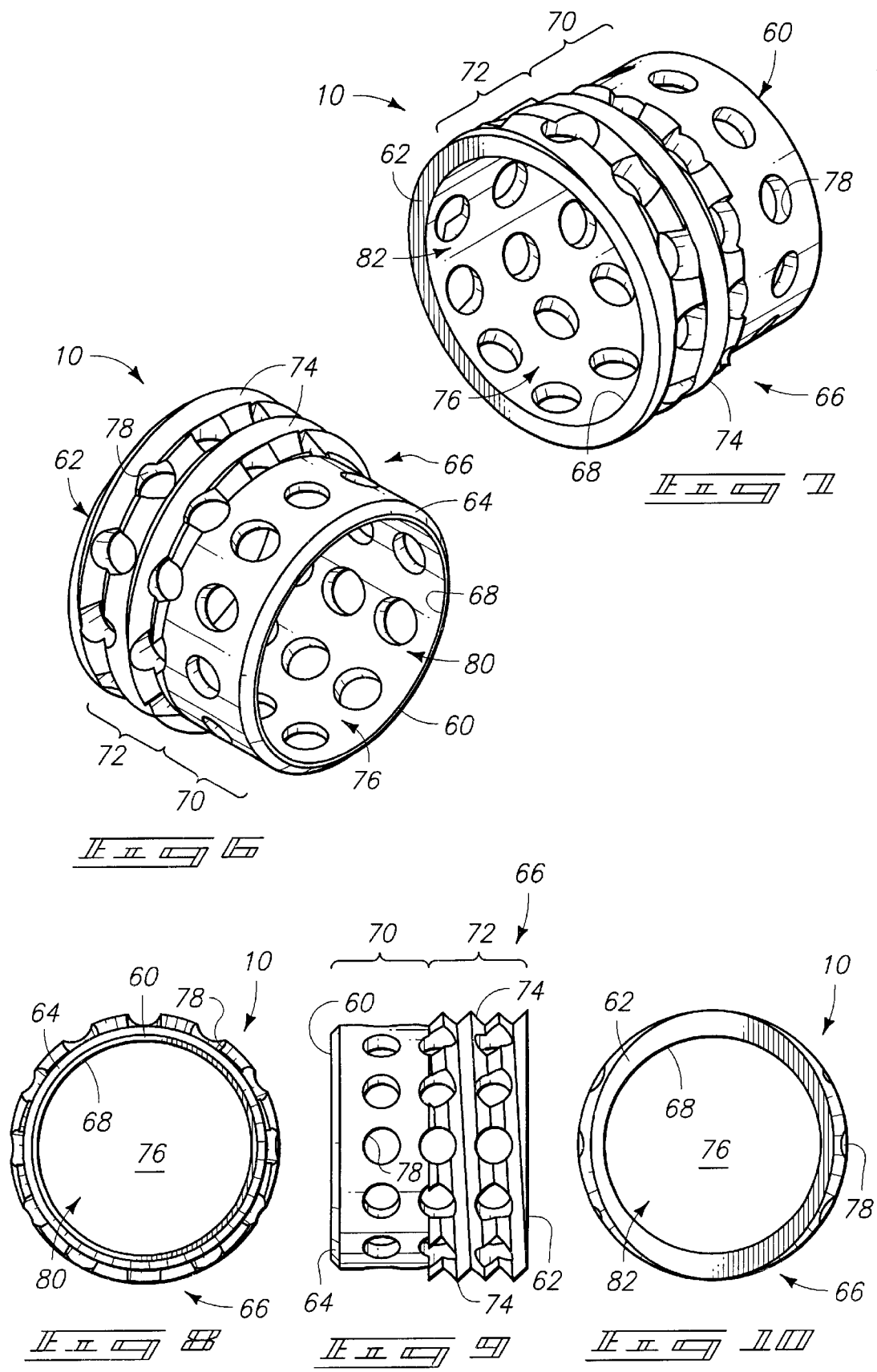

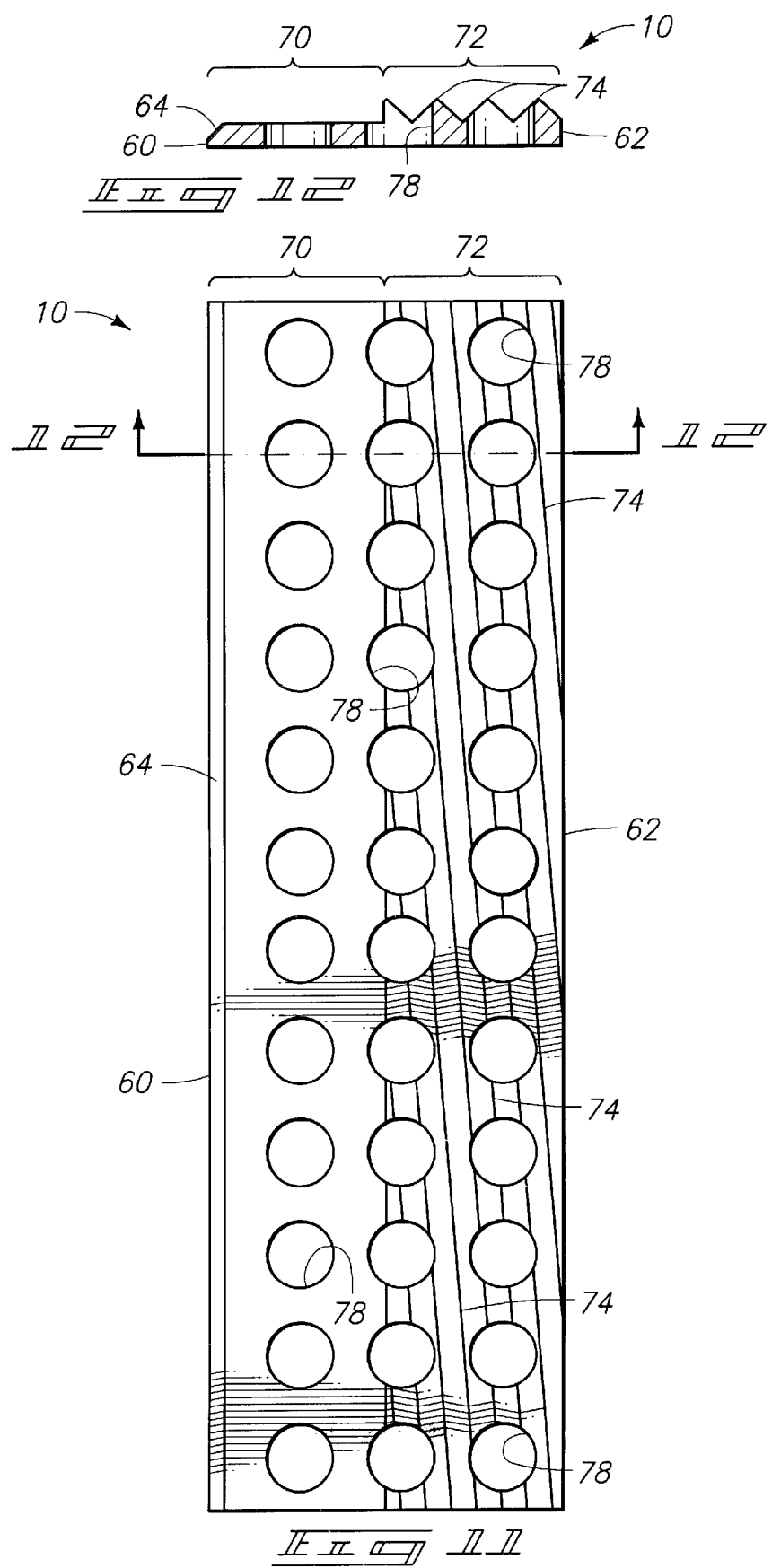

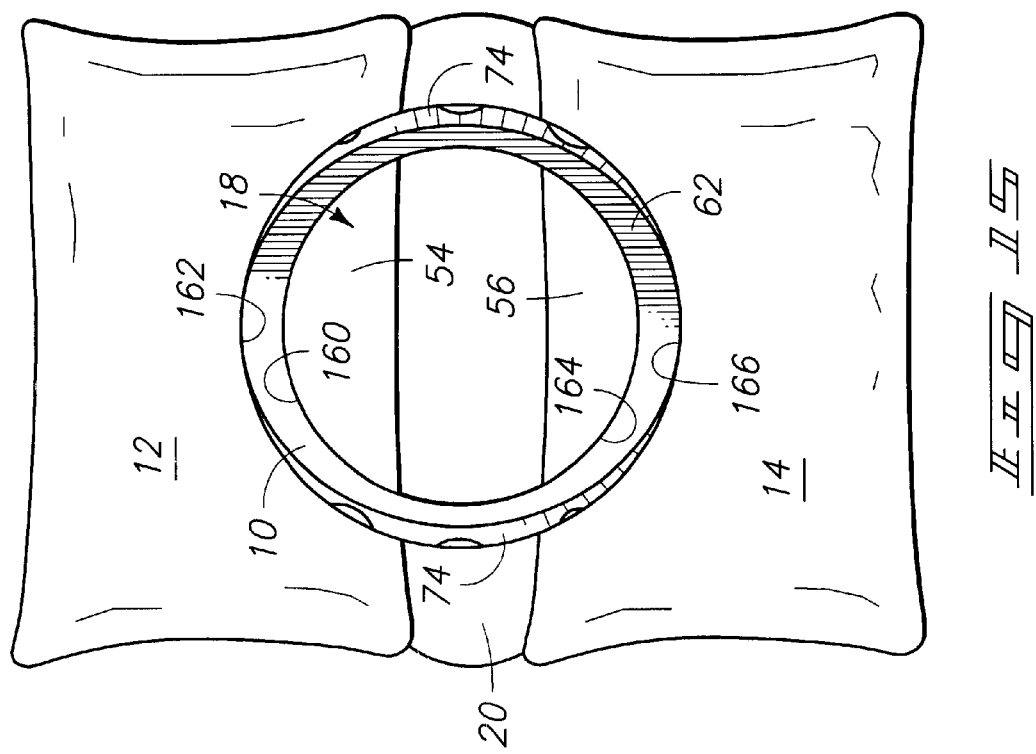
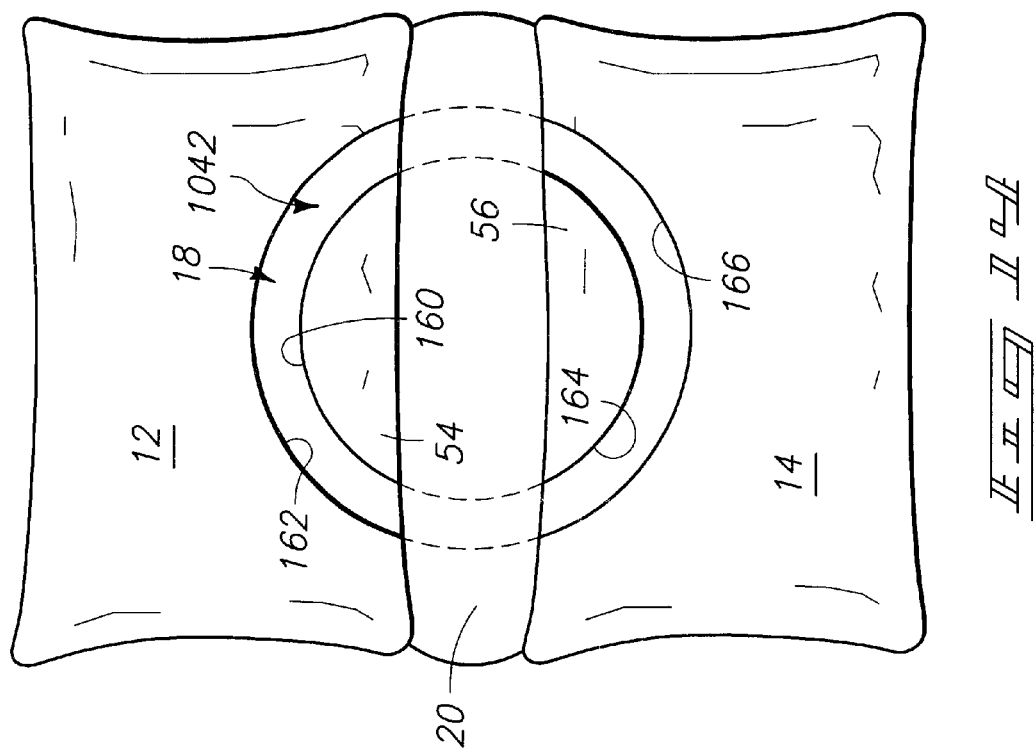

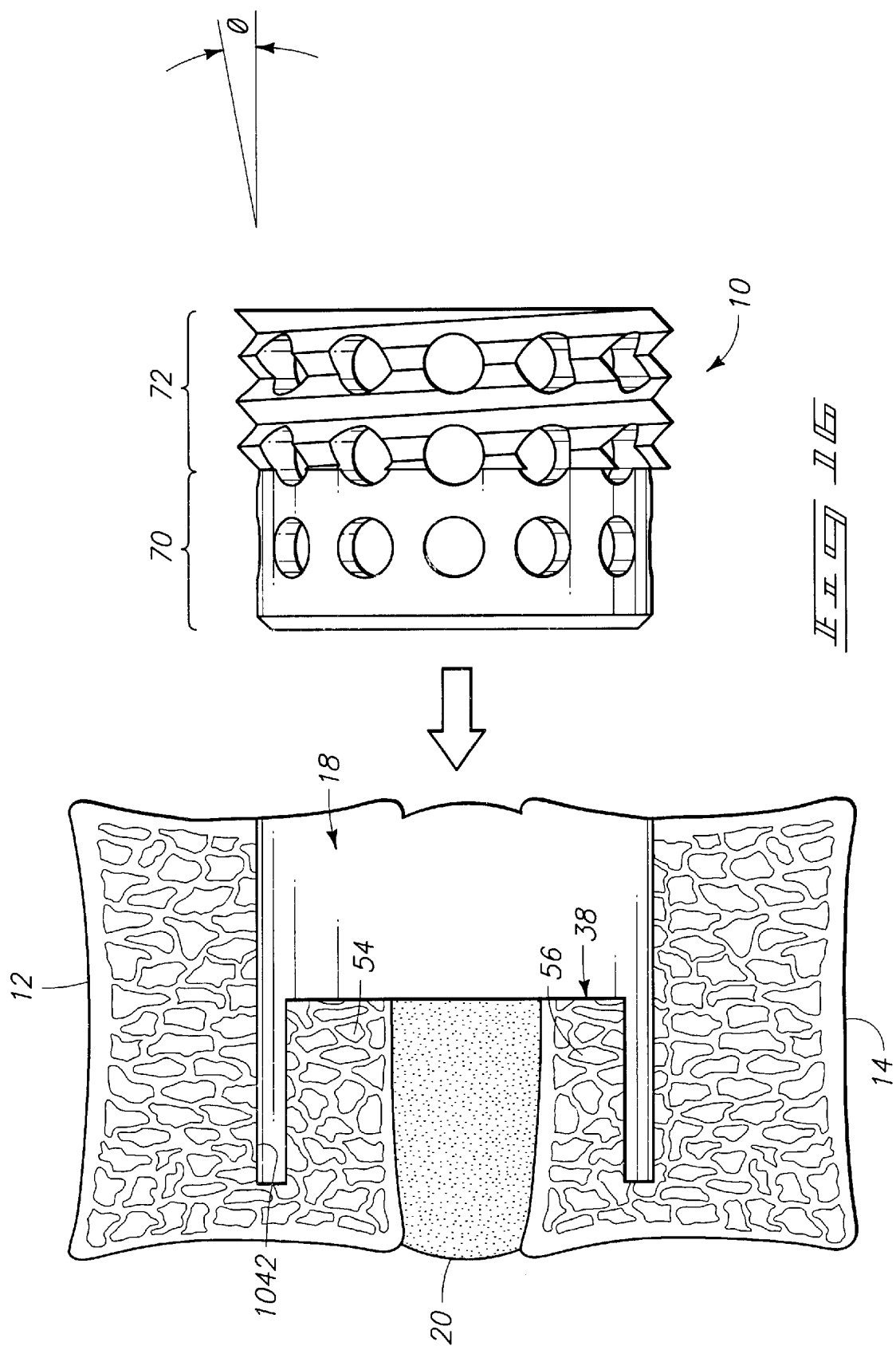

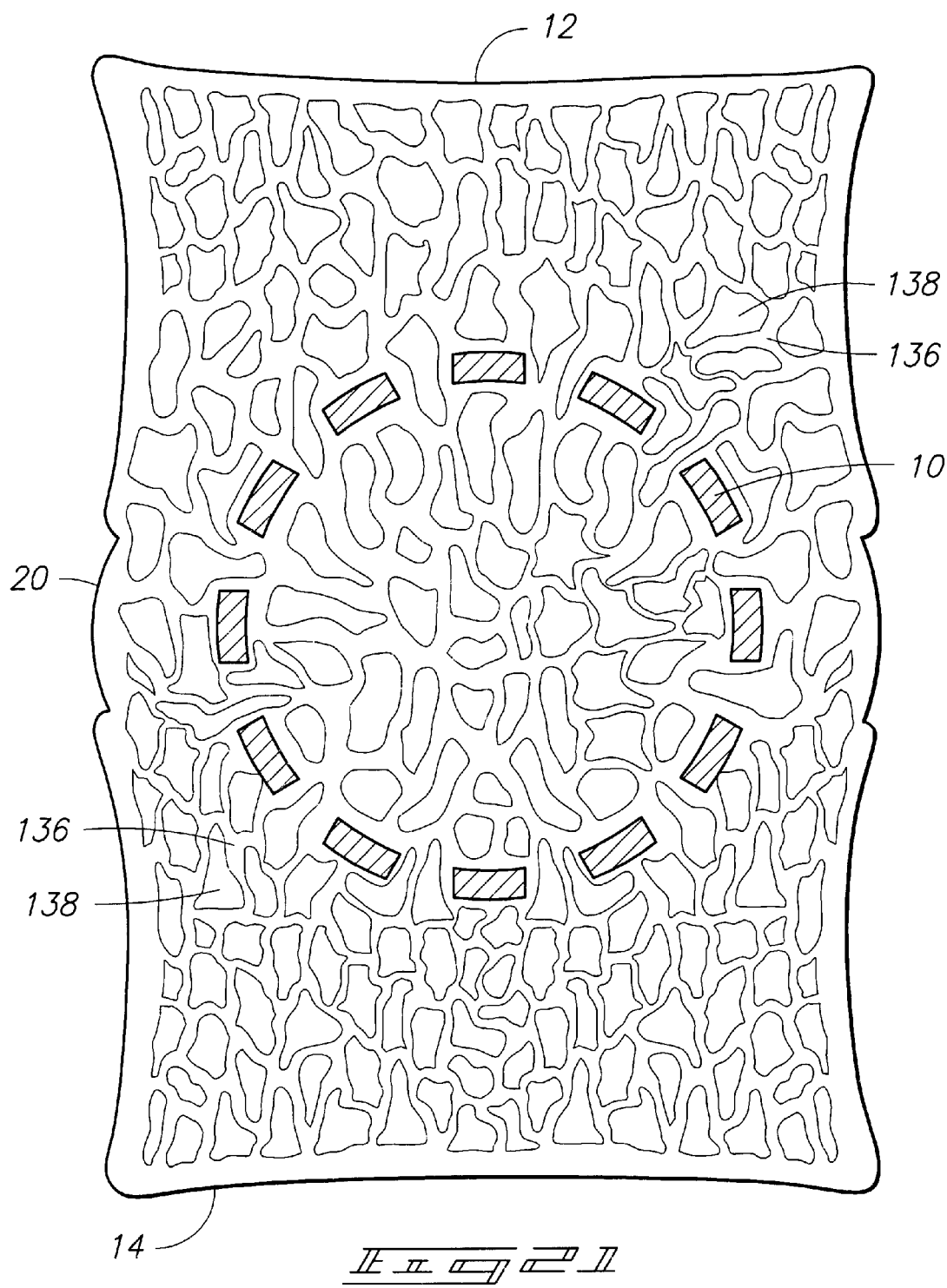

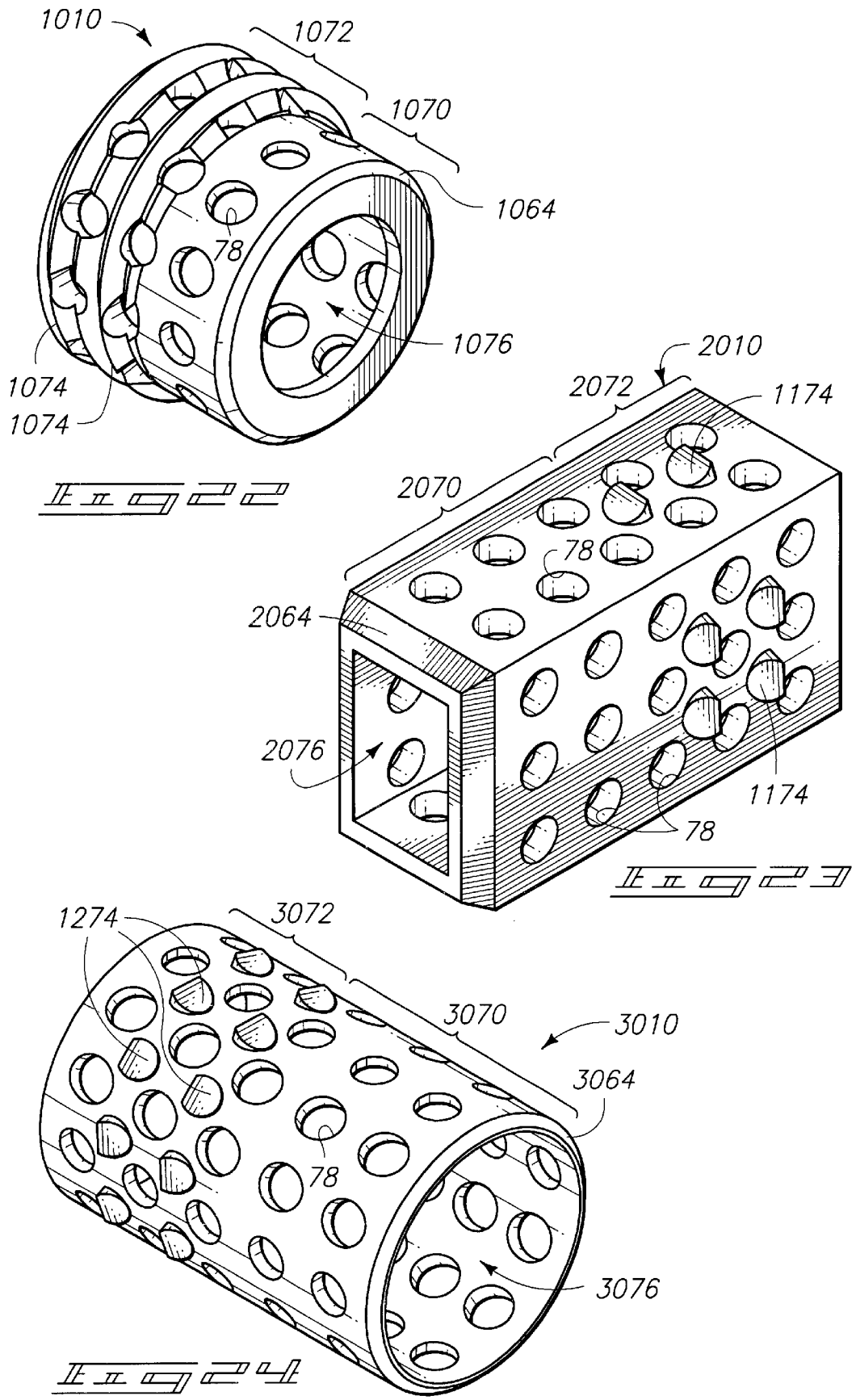

SELF-ALIGNING BONE IMPLANT

TECHNICAL FIELD

This disclosure relates to surgical joining of bone bodies, and more particularly to instruments, implants and methods for self-alignment, instant fixation and staged bone fusion or arthrodesis of bone bodies, such as spinal vertebrae.

BACKGROUND OF THE INVENTION

This invention was specifically developed for the surgical joining of is bone bodies, such as the fusing of contiguous spinal vertebrae so as to stabilize and prevent relative motion often resulting from a degenerative disc condition. Although the immediate effort leading to this disclosure is directed toward the lumbar, thoracic and cervical spine (anterior or posterior in approach), the described vertebral implants for immediate fixation and staged stabilization leading to arthrodesis (bone fusion) of bone bodies may be used in a bone fracture or osteotomy to fuse together resulting bone bodies, and across one or more joints or articulations. Furthermore, the implants may be used in the lumbar, thoracic and cervical spine.

The use of fixation plates and screws to hold together disunited bone bodies has long been known to facilitate arthrodesis or bone-to-bone union, such as bone fusion, and healing of fractured bones. Typically, the separate bone bodies are formed when a single bone fractures, requiring bone reunion. Plates are secured across a fracture region with screws, joining together the bone bodies. The plates hold the bone bodies together in proximate relation, facilitating bone growth s[ a]nd fusion therebetween. In this manner, the bone bodies are supported in close proximity, or in direct contact which facilitates fusion therebetween. However, these techniques are not practical for certain joints such as joints formed between spinal vertebrae. Therefore, a significant number of stabilizing implants have been designed for joining so together contiguous vertebrae.

One early technique for achieving arthrodesis between adjacent vertebrae across a joint or articulation is the well-known Cloward Technique for use in the human cervical spine. A solitary dowel of bone is tapped into place in a prepared circular bed that is smaller than the dowel of bone. The dowel acts as a wedge, distracting the surrounding soft tissues of the joint, and separating the bone bodies or vertebrae joined there along. The intervertebral disc substantially comprises the soft tissues of the joint. The dowel of bone is inserted, or wedged into place, providing its own stability by putting an annulus of the disc on stretch. Additionally, simple friction of the inserted dowel between adjacent vertebral bodies stabilizes axial dislocation. However, a second surgical procedure must be performed to extract or harvest the dowel of bone, substantially adding trauma to the procedure, increasing costs, as well as increasing the threat of infection to the patient. Alternatively, bank bone from human donors can be used, but bank bone is less osteogenic and may introduce infection, or even transmission of Acquired Immune Deficiency Syndrome (AIDS) or hepatitis. Furthermore, bone morphogenic protein, hydroxy apatite, or other bone stimulating material may be utilized. Additionally, there has been a need to ensure the implant remains axially secured which has lead to further developments.

A step forward from the Cloward Technique was provided by Bagby (U.S. Pat. No. 4,501,269) wherein a metal dowel uses the same principle. A perforated cylindrical hollow implant is inserted between prepared surfaces across a vertebral joint. The inserted implant immediately stabilizes the joint by spreading the bony surfaces apart in wedged opposition to surrounding tissue. This initial stabilization is more substantial because a metal dowel, unlike a bone dowel, will not be absorbed or fatigue in use. Over time, fusion occurs through and around the implant which is filled with bone fragments. Use of the metal dowel eliminates the need for a second operation to harvest a dowel of bone. Bone fragments to be inserted in the implant are retrieved during preparation of the circular beds in each vertebra. Furthermore, such a metal implant avoids the disadvantage of having to use bone bank to obtain donor bone. The Bagby implant described in U.S. Pat. No. 4,501,269 has a smooth outer surface, interrupted only by numerous openings or fenestrations through which bone ingrowth and through growth can occur. Ends of the implant are substantially closed, with one end receiving an end cap such that bone fragments are contained therein. Bone morsels or bone grafts are typically harvested when preparing the circular bed in each vertebra, after which they are placed into the fenestrated metal cylindrical implant. The Bagby implant is then driven or tapped into place in a manner similar to the placement of Cloward's Bone Dowel, which was solely directed for use in the cervical spine. However, the original Bagby implant relies completely upon stretch of the annulus to stabilize the vertebrae during bone remodeling and fusion.

Improvements have also been made to "Cloward's Technique" wherein two dowel bone grafts are posteriorly inserted (Wiltberger's Technique) between adjacent lumbar vertebral bodies. Furthermore, threaded surfaces have been added to such bone grafts in order to keep the grafts in place (Otero-Vich German Application Number 3,505,567, published Jun. 5, 1986). More recently, a number of U.S. Patents have proposed combining the threaded features from threaded bone grafts with a metal implant, resulting in rigid threaded implant structures for placement between adjacent spinal vertebrae.

One threaded metal fusion implant disclosed in Michelson (U.S. Pat. No. 5,015,247) provides a cylindrical fusion implant having an outer diameter sized larger than the space between adjacent vertebrae to be fused. Threads provided on the exterior of the member engage the vertebrae to axially secure the implant therebetween. The implant has a plurality of openings configured along the cylindrical surface to promote bone ingrowth. However, the threads per se of the implant do not function as a fastener to fix together the adjacent vertebral bodies. Instead, the implant functions as a wedge, imparting a distraction force across the disc which stabilizes the articulation formed therebetween by stretching the annulus of the disc. In fact, the threaded implant relies solely on the annulus to provide stabilization between the vertebrae, in direct response to wedge-induced distraction created therebetween. Distraction of the annulus stabilizes the two vertebrae, enabling ingrowth to later occur within the implant. Therefore, through-growth and fusion (arthrodesis) occur between the adjacent vertebrae subsequent thereto depending on the immobilizing potential of an intact healthy annulus which may or may not be present.

Several additional problems result from the provision of threads on a cylindrical fusion implant. One significant problem with threaded metal fusion implants is that it is very difficult to thread the implant into alignment with prepared bone beds in adjacent vertebral bodies. In practice, such alignment can prove difficult, and the consequences of misalignment can detrimentally affect the ability to achieve fusion between the vertebral bodies and the ability to subsequently achieve arthrodesis. Aligned placement of such an implant is likely to lead to a higher incidence of arthrodesis. Additionally, for cases where a fusion implant does not have a physical retention mechanism for retaining the implant between bone beds, such implant may not be sufficiently mobilized to prevent movement. Such movement will also detrimentally affect the successful incidence of arthrodesis. Yet another problem results in that threads take up additional space which can make implantation in areas having limited anatomical space very difficult, such as in the posterior approach in the lumbar spine. Additionally, the threads effectively make the wall thickness greater which further separates bone provided inside the implant with bone provided outside the implant, which can delay initial bone union.

For bone fusion to occur with any of the above devices, the invasion of new delicate blood vessels from the adjacent healthy bone is necessary for the creation of new living interconnecting bone. Where complete stabilization does not occur instantaneously upon implantation, motion can disrupt the ingrowth of delicate blood vessels. Disruption of the vessels then restricts or even prevents bone healing therebetween. The same problem occurs with any of the abovementioned implant techniques, including the threaded techniques of Otero-Vich and Michelson. Even when the annulus is completely on stretch, the threads per se of these constructions do not function in the manner of conventional screws, extending through one object and into another. Namely, they do not function to fasten together adjacent bodies by coaction of the implant with each body. For example, the threads merely act as a series of ridges that engage with each adjacent bone body, while the implant body functions as a wedge. The implant distracts apart the vertebral bodies which stretches the annulus, and stabilizes the articulation as a consequence thereof, while the thread functions solely to prevent axial dislodgement. Furthermore, the presence of threads requires the implant to be screwed in place via a torquing process, instead of tapping the implant directly into position.

Hence, some recent designs have resulted in an implant that produces immediate fixation per se between bone bodies following insertion and independent of the annulus. Such designs show promise particularly for cases where the annulus structure is substantially or completely weakened or damaged at surgery. Where the annulus is damaged so significantly as to lose structural integrity, the wedge-effect of prior art threaded implants will not produce any distraction forces across the annulus. Also, when the implant is used to arthrodese and change angulation, a healthy annulus cannot be totally corralled to be placed on stretch. As a result, there is no form of stabilization or fastening between bone bodies sufficient to enable the occurrence of arthrodesis therebetween when the annulus is weakened or inadequate. Additionally, there exist additional shortcomings with such recent designs as discussed below.

One such design that produces immediate fixation is disclosed in Bagby (U.S. Pat. No. 5,709,683) as a bone joining implant having a spline or undercut portion that engages in assembly with each bone body to be joined. However, such design requires the preparation of bone beds that are engaged in interlocking relation with a bone bed engaging portion provided by such undercut portions.

Many of the previously described implants can be inserted between vertebrae while such vertebrae are distracted with a distraction tool. One such tool uses a threaded pin which is inserted laterally into each bone body, with such pins being rigidly secured therein. Such tool distracts the vertebrae by separating the pins and vertebrae which stretches the annulus. A drill is then used to drill out bone beds within the vertebrae, after which the implant is inserted therein. However, such procedure does not always impart sufficient distraction and takes time and space to implement. Therefore, techniques that provide further distraction are desired.

For the case of vertebral inner body implants which lack the presence of any external threads, the implant is typically tapped into place between bone beds prepared in adjacent vertebral bodies. However, complete tapping of such an implant extending in an anterior to a posterior direction can be somewhat risky as the leading end of the implant is the spinal cord. Accordingly, improvements are desired to minimize any risks resulting from completely tapping an implant into place between pairs of adjacent vertebral bodies.

Therefore, there is a present need to provide an implant device that more accurately aligns itself with prepared bone beds between bone bodies upon implantation, enhances arthrodesis by encouraging bony fusion adjacent the implant, and ensures retention between adjacent bone bodies during insertion. There is also a need to provide such a device that facilitates accurate aligned placement and staged stabilization leading to bone fusion, in a manner that is relatively simple, more reliable, less complicated, has fewer parts, and leads to quicker and more thorough bone fusion and remodeling therebetween. The final stage of bone fusion through and around the implant substantially eliminates any need for the implant to maintain the fusion, thus allowing the bone union to provide primary support therebetween.

SUMMARY OF THE INVENTION

A self-aligning, self-fixating, and self-distracting vertebral fusion device is disclosed according to four distinct embodiments. Although not necessary, an additional feature is provided by less than all of the embodiments which encompasses bone joining features that entrap bone projections to instantly fix adjacent bone bodies together, such as instantly fixing adjacent vertebral bodies via the implant.

According to one aspect of the invention, a bone joining implant includes a tubular body. The tubular body has an axially extending outer surface defining an outer dimension of substantially uniform cross-section and including a smooth leading insertion portion and a bone engaging trailing portion.

According to another aspect of the invention, a vertebral fusion device includes a perforated fusion body. The perforated fusion body has an insertion portion with an axially extending uniform cross-sectional dimension adjacent a leading end and a bone fixating trailing portion adjacent a trailing end.

According to a third aspect of the invention, a vertebral fusion implant includes an elongate, axially extending fusion body. The fusion body includes an insertion portion having an axially extending uniform cross-section and a threaded trailing portion provided at a trailing end of the fusion body. The insertion portion self-aligns the fusion body with bone beds of adjacent vertebrae during implantation. The threaded trailing portion self-fixates the fusion body between the bone beds.

According to a fourth aspect of the invention, a bone fusion device includes an axial extending body. The axial extending body has a cylindrical leading end portion communicating with a threaded trailing end portion. The threaded trailing end portion includes at least one thread segment extending radially outwardly of an outermost surface of the cylindrical leading end portion.

BRIEF DESCRIPTION OF THE DRAWINGS

Preferred embodiments of the invention are described below with reference to the following accompanying drawings.

FIG. 5 is a perspective view of a kerf cleaning/deburring tool for further widening the kerf produced in FIG. 4 and cleaning debris from the cylindrical kerf formed within the vertebral bodies;

FIG. 6 is a perspective view taken from the leading, insertion end of the vertebral interbody implant of FIG. 1 for insertion within the prepared bone beds of FIG. 5;

FIG. 7 is a perspective view taken from the driven end of the vertebral interbody implant of FIG. 6;

FIG. 9 is a side view of the vertebral interbody implant of FIGS. 6 and 7;

FIG. 8 is a leading end view of the vertebral interbody implant of FIGS. 6–8;

FIG. 10 is a driven end view of the vertebral interbody implant of FIGS. 6–9;

FIG. 11 is an unrolled plan view of the outer peripheral surface of the vertebral interbody implant of FIGS. 6–10;

FIG. 12 is sectional view taken along line 12—12 of FIG. 11 further illustrating the smooth leading end and the threaded, retaining trailing end of the vertebral interbody implant of FIGS. 6–11.

FIG. 14 is a simplified frontal view illustrating a pair of vertebrae that have bone beds prepared according to the steps depicted in FIGS. 2–5 comprising a cylindrical kerf;

FIG. 15 is a simplified frontal view illustrating the vertebrae of FIG. 14 in an instantly fixed and slightly distracted position caused by inserting the implant of FIGS. 6–10 within the bone beds of FIG. 5;

FIG. 16 is a simplified, sagittal and centerline view of the implant of FIGS. 6–13 prior to insertion.

FIG. 21 is a coronal view of the implant and healed bone comprising vertebrae and taken along line 21—21 of FIG. 20 and showing arthrodesis;

FIG. 22 is a perspective view of an alternatively constructed vertebral interbody implant similar to the embodiment depicted in FIGS. 1–21 for insertion within prepared bone beds formed solely by generating a bore as shown in FIG. 2; and FIG. 23 is a perspective view of an alternatively constructed vertebral interbody implant similar to the embodiment depicted in FIGS. 1–21 for insertion within prepared bone beds formed solely by generating a bore as shown in FIG. 2.

FIG. 24 is a perspective view of an alternatively constructed vertebral interbody implant similar to the embodiment depicted in FIGS. 1–21 for insertion within prepared bone beds formed solely by generating a bore as shown in FIG. 2.

DETAILED DESCRIPTION OF THE PREFERRED EMBODIMENTS

Figure 1:
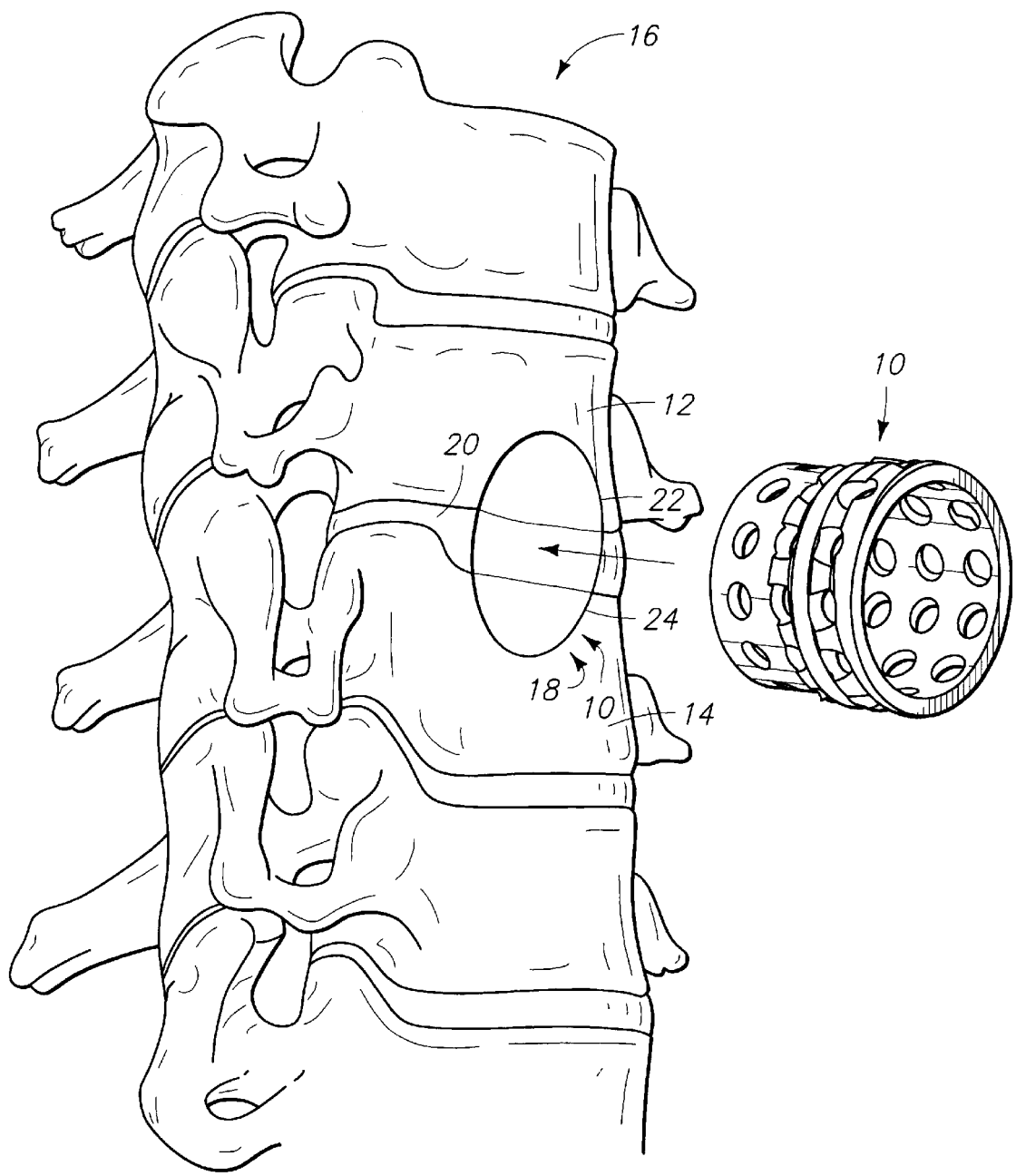
FIG. 1 is a perspective view of a vertebral structure showing a vertebral interbody implant embodying this invention.

This disclosure of the invention is submitted in furtherance of the constitutional purposes of the U.S. Patent Laws "to promote the progress of science and useful arts" (Article 1, Section 8).

Reference will now be made to a preferred embodiment of Applicant's invention. Four exemplary implementations are described below and depicted with reference to the drawings comprising various self-aligning and self-fixating bone joining implants. A first embodiment is shown and described below in a first mounting configuration with reference generally to FIGS. 1–21. Second through fourth embodiments are shown and described below with reference to FIGS. 22–24, respectively. While the invention is described by way of several preferred embodiments, it is understood that the description is not intended to limit the invention to these embodiments, but is intended to cover alternatives, equivalents, and modifications which may be broader than these embodiments such as are defined within the scope of the appended claims.

In an effort to prevent obscuring the invention at hand, only details germane to implementing the invention will be described in great detail, with presently understood peripheral details being incorporated by reference, as needed, as being presently understood in the art.

A preferred embodiment bone joining implant in accordance with the invention is first described with reference to FIGS. 1, 6–13 and 15–21. Such an implant is further described below with respect to a cylindrical, open-ended vertebral inter-body implant having self-aligning and self-fixating features. Additionally, an optional feature includes a leading open end in the form of a cylindrical inner surface that entraps bone projections, and a tapered leading end that provides limited self-satisfaction. The self-aligning and self-fixating implant is designated in FIGS. 1, 6–13 and 15–21 generally with reference numeral 10.

A first alternative implementation comprising a cylindrical vertebral inter-body implant similar to implant 10 above, but with a pair of end flanges and a central bulkhead flange, is depicted in FIG. 22. A second alternative implementation comprising a tubular, rectangular cross-section implant with a plurality of retaining tabs provided about a trailing surface portion is depicted in FIG. 23. A third alternative implementation comprising a cylindrical vertebral inter-body implant with a smooth leading outer surface portion and a plurality of retaining tabs provided about a trailing surface portion is depicted in FIG. 24.

As shown in FIGS. 1, 6–13 and 15–21, implant 10 comprises a rigid, unitary body having a cylindrical leading edge 60 and a cylindrical outer surface 66, with an open leading end 80 (see FIGS. 6–10). As shown in FIG. 1, implant 10 is inserted within an aperture 18 that has been prepared between a pair of adjacent vertebral bodies 12 and 14 within a vertebral column 16.

As shown in FIG. 1, aperture 1B is prepared within vertebral bodies 12 and 14, and along disc 20, according to the procedure and tools depicted in FIGS. 5–11 and described below in further detail. Aperture 18 forms a pair of vertebral bone bodies 22 and 24 that are formed to have a cylindrical configuration comprising a cylindrical kerf 1042 (see FIGS. 14, 16 and 17). A leading cylindrical end of implant 10 is inserted into aperture 18, causing vertebral bodies 12 and 14 to be instantly fixed together (see FIGS. 14–18 below). An open leading end 80 (see FIG. 6) of implant 10 entraps an intact living bone projection 54 and 56 on each respective vertebral body (see FIGS. 14–18) which imparts immediate fixation between adjacent vertebral bodies 12 and 14 upon implantation.

More particularly, vertebrae 12 and 14 comprise neighboring bone bodies of a vertebral column 16 (see FIG. 1). A resilient articulation or joint is formed between vertebra 12 and 14 by disc extending between vertebrae 12 and 14. Anatomically, the disc is made up of a central nucleus pulposus and an outer encircling annulus. The annulus and nucleus pulposus are composed of laminae of fibrous tissue and fibro-cartilage. The nucleus pulposus, located at the center of the disc, comprises a soft, pulpy, and highly elastic substance. The annulus is formed from laminae of fibrous tissue extending in a crisscrossing fashion to encircle the nucleus pulposus. Additionally, the intervertebral disc is adherent, by its cephalad and caudad surfaces, to a thin layer of hyaline cartilage that covers the top and bottom surfaces of adjacent vertebras. In a healthy patient, adjacent vertebra 12 and 14 are spaced apart by disc 20. However, degenerative disc disease and localized trauma can cause degradation or complete loss of the soft tissue components between neighboring vertebrae. For example, the annulus can partially or completely tear which can seriously degrade the structural condition of the articulation. Additionally, fluid can escape from the nucleus pulposus. When any of the above happens, vertebrae 12 and 14, loaded by the normal weight bearing of a patient, are pressed into closer adjoining positions, which can result in pinching of nerves that extend from between vertebrae of the spinal column (not shown), Therefore, there is a need to recover the disc spacing provided by a normal healthy disc 20 by way of inserting implant 10. Furthermore, there is a need to provide implant 10 with a fixation that aligns implant 10 during insertion and instantly interlocks adjacent vertebra 12 and 14 together upon being implanted. Furthermore, there is a need for such an implant 10 that retains itself in place upon insertion, and that facilitates staged stabilization resulting in arthrodesis to occur between the vertebral bodies, following initial implantation. Even furthermore, there is a need to instantly fix adjacent vertebrae together since relative motion can otherwise cause pinching of nerve tissue.

As a result, implant 10 can be inserted, preferably in a central location between adjacent vertebrae 12 and 14 of patients who have bad, ruptured or degenerative discs. Furthermore, implant 10 can be axially oriented anterior to posterior, or even laterally.

In summary, implant 10 is adapted for implantation between prepared bony surfaces or beds 22 and 24 and across the articulation formed by disc 20. A typical implantation might involve placement of one or more implants 10 as required in order to stabilize and fix the joint during bone ingrowth and through-growth of the implant structure. Bone growth is also accomplished outside of and surrounding the implant.

Alternatively, a pair of somewhat smaller sized and laterally adjacent implants can also be used. However, such dual implant implementation uses individual implants that are sized smaller than the single implant 10 of FIG. 1. As a result, such dual implant implementation uses smaller sized apertures which do not invade as much cancellous bone as the aperture 18 (see FIG. 1) prepared for receiving the larger sized single implant implementation depicted in FIG. 1.

A solitary implant 10 as shown in FIG. 1 invades cancellous bone since aperture 18 has a larger diameter. In contrast, smaller sized dual implants tend to invade mostly cortical bone on the end plates. However, cancellous bone is more desirable for bone growth during staged bony fusion since cancellous bone is more osteogenic than cortical bone. New growth bone, or callus bone, comprises soft cancellous bone that only becomes hard (cortical) over time via action of Wolff's Law of maturity.

Applicant's implant depicted in FIGS. 6–10 generates a limited amount of self-distraction during insertion between a pair of vertebral bodies due to tapered portion 64. Such feature provides an additional desirable benefit.

FIGS. 2–5 illustrate the various steps used to prepare aperture 18 and bone beds 22 and 24 within vertebral bodies 12 and 14, respectively (of FIG. 1). Such figures illustrate one technique for preparing a suitable pair of bone beds within adjacent vertebrae 12 and 14 for receiving implant 10 (of FIG. 1) such that self-alignment, self-fixation, self-distraction and immediate fixation are imparted between vertebral bodies 12 and 14.

Figure 2:
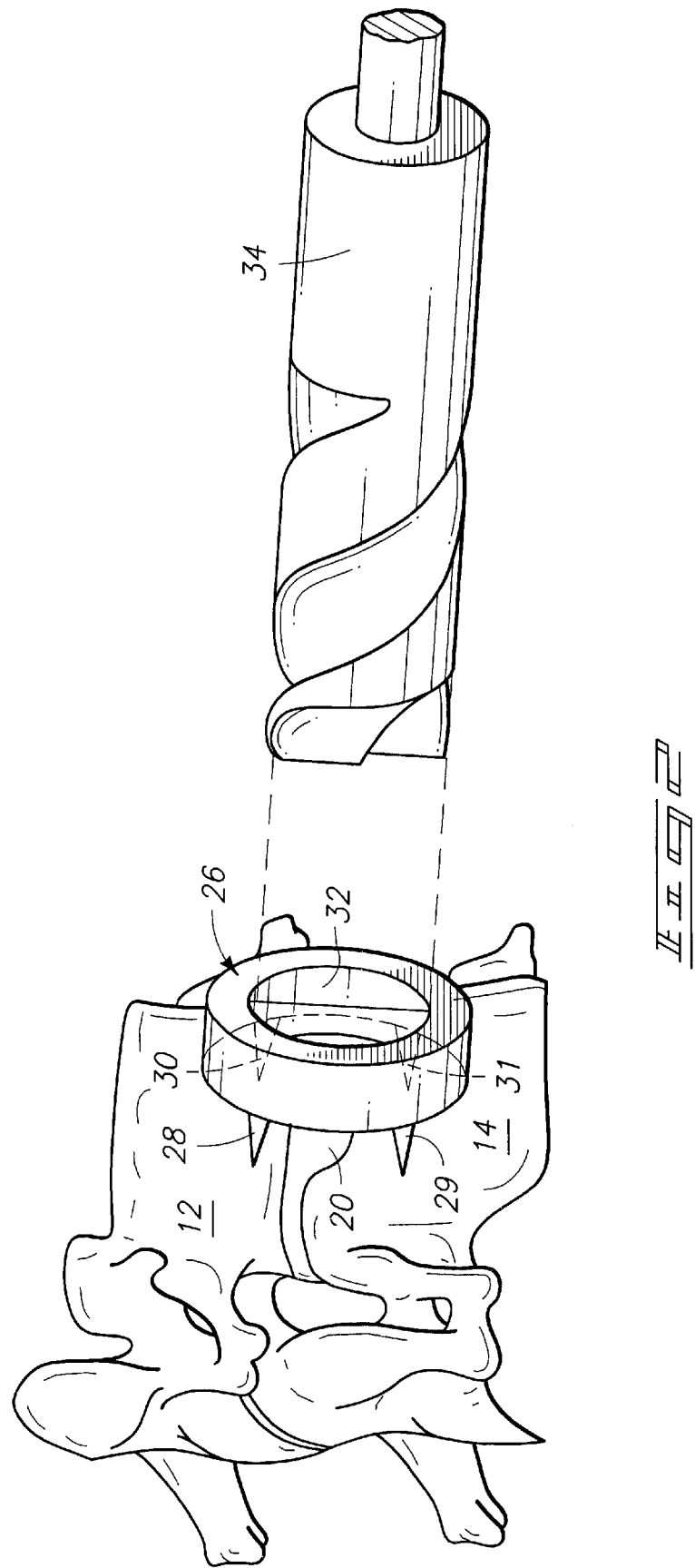
FIG. 2 is a perspective view of a pair of adjacent vertebrae and illustrating a drill guide and drill bit used to prepare a bore that initiates preparation of bone beds within the vertebrae.

FIG. 2 depicts a tool guide 26 and a drill bit 34 that are used to drill a bore 38 (see FIGS. 3–5) into vertebral bodies 12 and 14 and disc 20. Bore 38 is drilled partially into bodies 12 and 14 so as to leave sufficient intact living bone to create bone projections 54 and 56 (see FIGS. 5 and 15–18) having sufficient size to impart instant fixation between bodies 12 and 14 upon insertion of implant 10.

As shown in FIG. 2, tool guide 26 is first tapped into engagement with vertebral bodies 12 and 14 by an alignment drive tool and hammer (not shown). Sharp fingers or projections 28–31 engage and enter the outer surfaces of bodies 12 and 14 which causes tool guide 26 to be rigidly and securely seated between bodies 12 and 14. In this position, a central bore 32 of tool 26 is aligned in an anterior/posterior direction. Bore 32 is sized to receive and guide a tool bit 34 in an anterior/posterior direction through bodies 12 and 14 and annulus 20.

Figure 3:
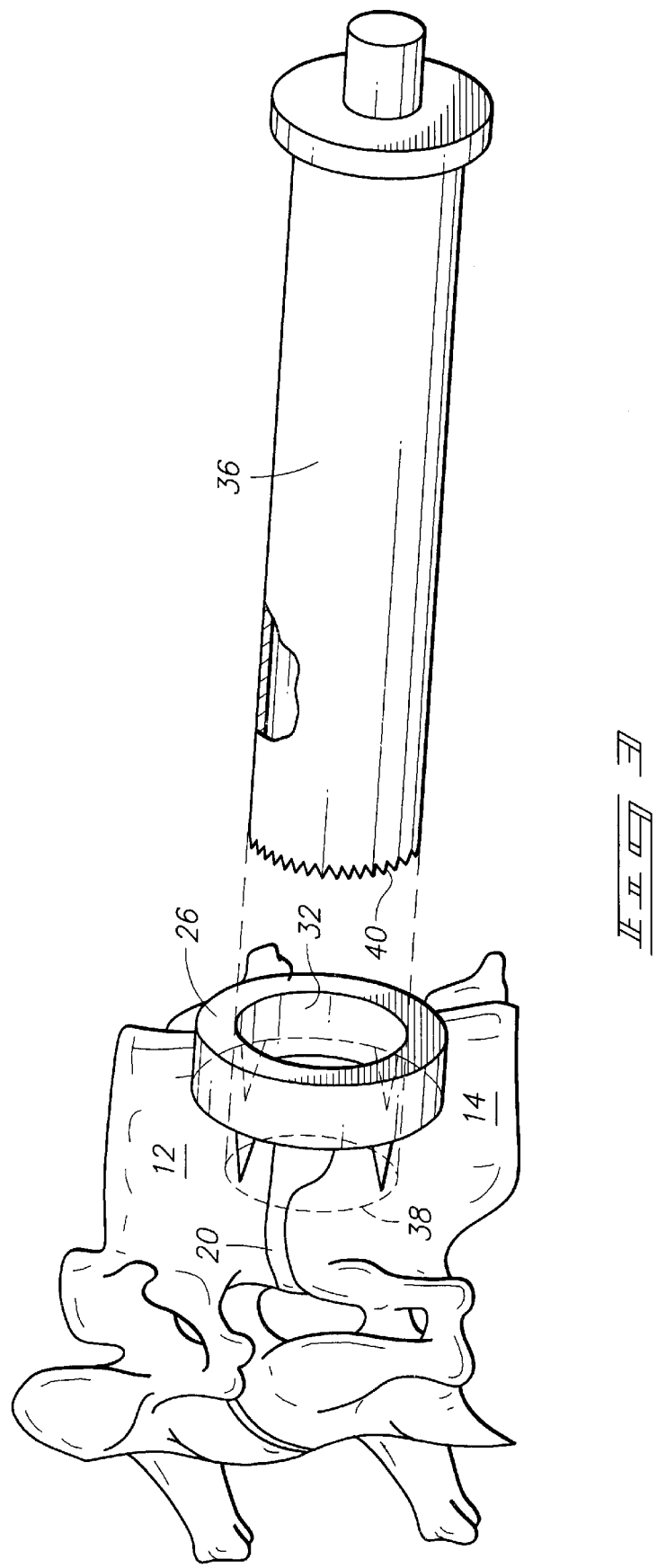
FIG. 3 is a perspective view of the pair of vertebrae of FIG. 2, and illustrating a first hole saw used with the drill guide to cut a cylindrical kerf about the bore in order to further prepare the bone beds within the vertebrae.
Figure 4:
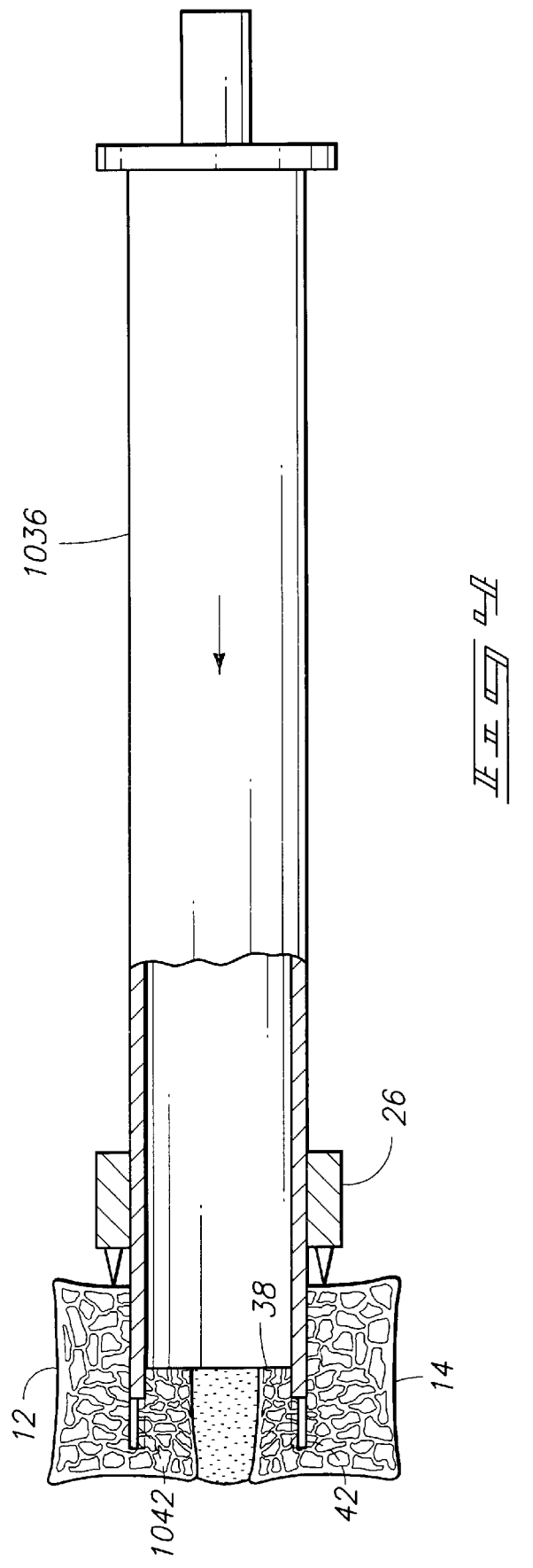
FIG. 4 is a simplified side view illustrating a second hole saw of FIG. 3 used to further cut a further widened cylindrical kerf within the pair of vertebrae.

More particularly, drill bit 34 is driven in rotation by a drill (not shown) so as to cut out bore 38 (see FIG. 3). One suitable drill comprises a Hudson hand-driven manual drill. Alternatively, a power drill can be used to drive drill bit 34. Typically, bore 38 is drilled with sufficient depth into bodies 12 and 14 to extend between 30–70% of the depth of cylindrical kerfs 42 and 1042 as shown in FIG. 4. After forming bore 38 with drill bit 34 of FIG. 2, kerfs 42 and 1042 are subsequently cut out in succession using the tools depicted with reference to FIGS. 3–5 as described below.

Figure 17:
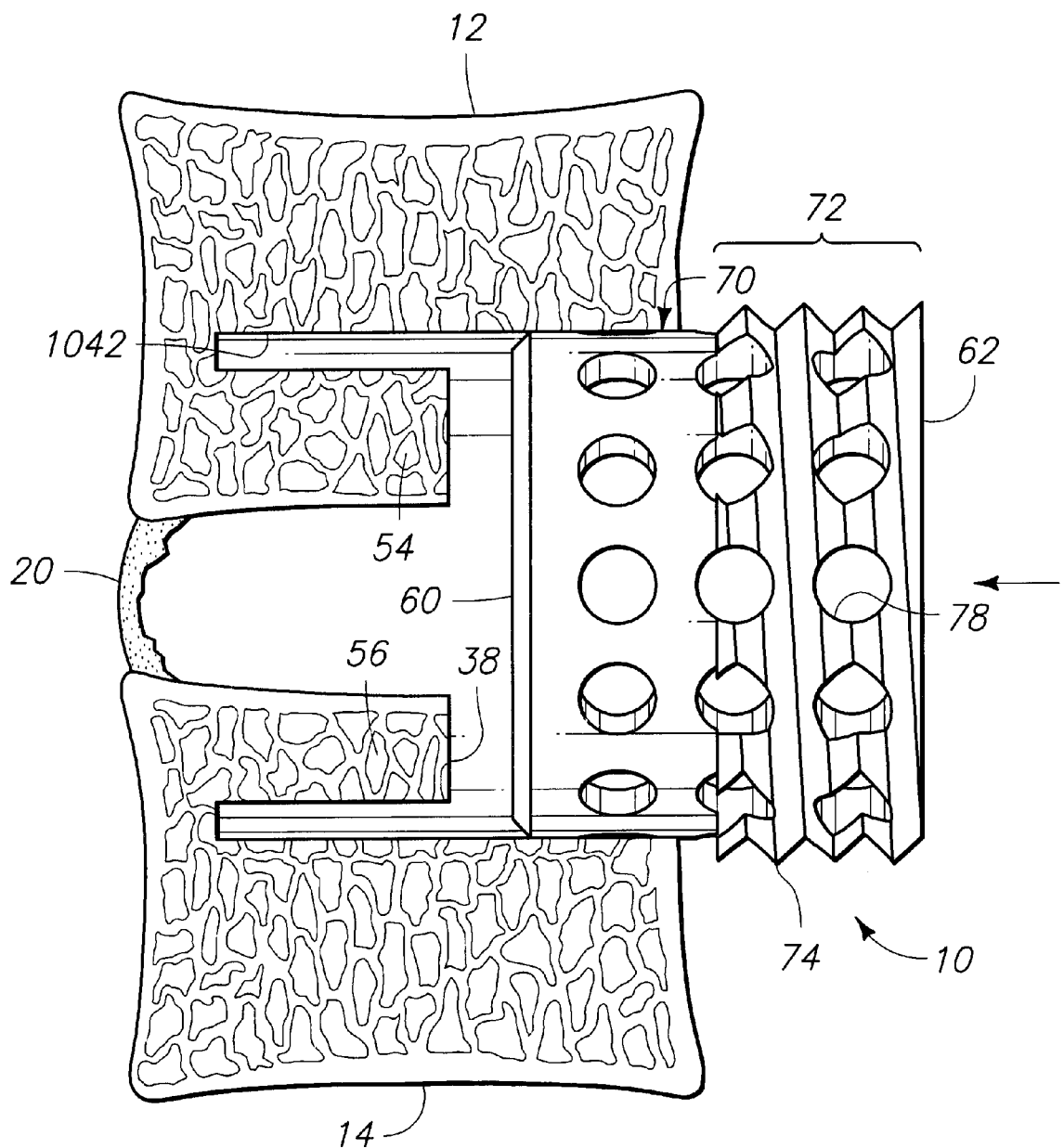
FIG. 17 is a simplified, sagittal and centerline view of the implant of FIGS. 6–13 during insertion.

FIG. 3 illustrates a first hole saw 36 used in combination with tool guide 26 to form cylindrical kerf 42 (see FIG. 4). As illustrated in FIG. 7, hole saw 36 is used to cut a cylindrical groove comprising kerf 42 (see FIG. 4) to a depth approaching 90%–100% of the finished depth of kerf 1042. Hole saw 36 is inserted into bore 38 such that a cylindrical groove is cut in axial alignment with bore 38. Thereafter, rotating cylindrical blade 1036 of FIG. 4 is used to cut or widen kerf 42 to achieve substantially 100% of the final depth and width of kerf 1042 as shown in FIGS. 14, 16 and 17.

Subsequently, a hand-driven kerf cleaning/deburring tool 44 is then used to clean debris 58 (see FIG. 5) from the cylindrical groove which prepares and finishes kerf 1042 therein. Optionally, hole saws 36 and 1036 of FIGS. 3 and 4, respectively, can be replaced with one or more rotary oscillating hole saws. Further optionally, final kerf 1042 can be formed solely by use of hand-driven tool.

As shown in FIGS. 3 and 4, hole saws 36 and 1036 each comprise a hollow saw blade having a shank that is driven in rotation by a drill (not shown). The cylindrical saw blade of hole saw 36 is inserted in bore 38 of tool guide 26 during a cutting operation as shown in FIG. 3. Guide 26 directs hole saw 36 to cut in an accurate anterior/posterior direction that is coaxial with bore 38 formed by drill bit 34 (of FIG. 2).

FIG. 5 illustrates one construction for a kerf cleaning/deburring tool 44 used to remove debris 58 from within the cylindrical groove of kerf 1042 formed between vertebral bodies 12 and 14. Tool 10 includes a t-shaped handle 46 and a hollow cylindrical cutting body 48 having an open end terminating in a plurality of circumferentially spaced apart cutting teeth 50. A deep gullet, or throat, 52 is provided between adjacent teeth 50 for collecting debris that is removed when tool 10 is inserted and rotated within the cylindrical groove of kerf 1042. Tool 44 is inserted into the groove while handle 46 is rotated back and forth to impart back and forth rotary movement to teeth 50 within kerf 1042. Debris 58 is removed and cut from kerf 1042 by movement of teeth 50. Such debris 58 lodges in gullets and within the hollow interior of body 48. Tool 46 is then removed from kerf 1042 which also removes debris 58. Furthermore, teeth 50 impart a final finished dimension to cylindrical kerf 1042 prior to inserting an implant therein.

Figure 18:
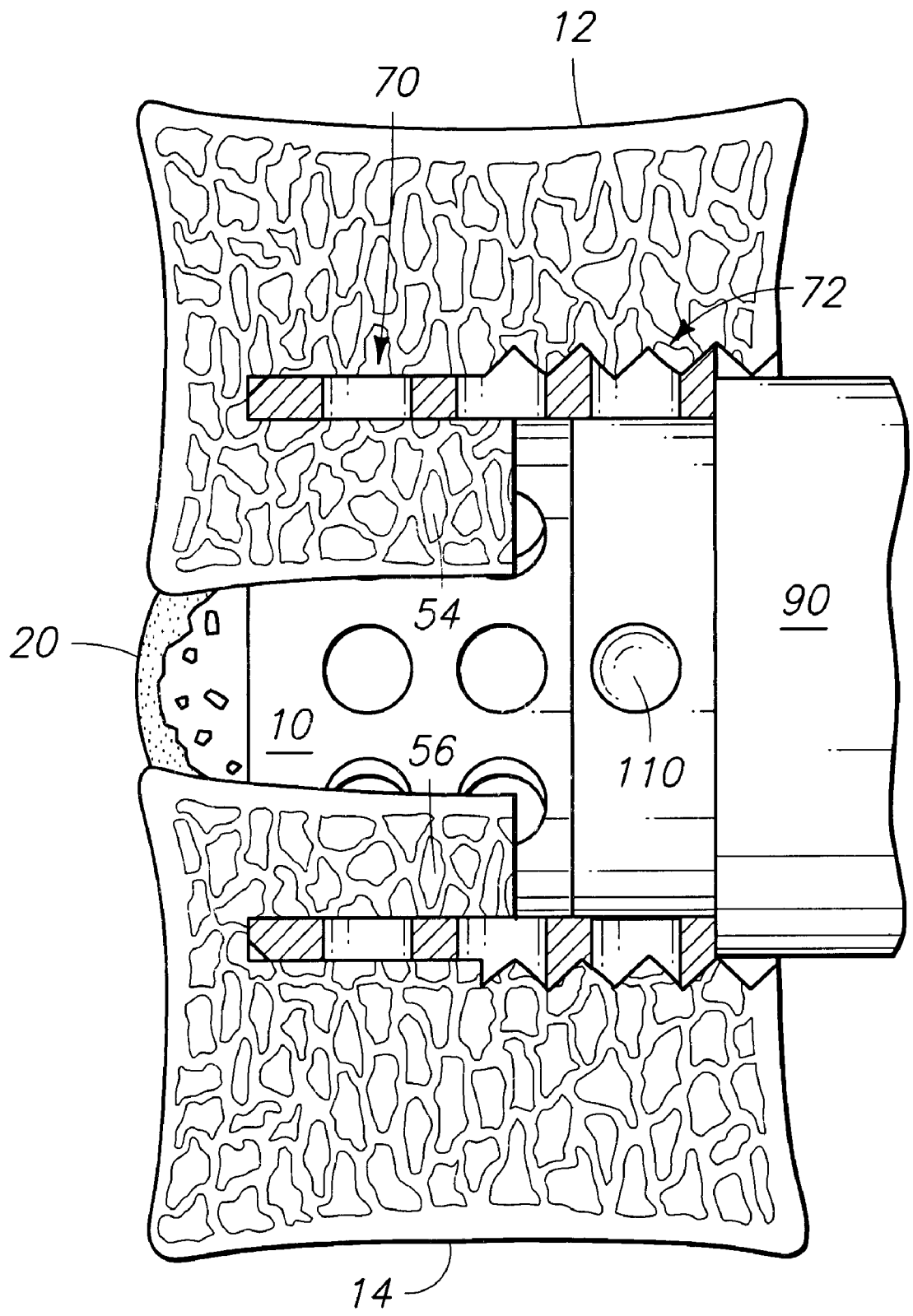
FIG. 18 is a simplified, sagittal and centerline view of the implant of FIGS. 6–13 after insertion.

FIGS. 6–12 illustrate self-aligning and self-fixating implant 10 in various perspective, side and end views. Implant 10 has a cylindrical leading edge 60 and a trailing edge 62. A cylindrical outer surface 66 and a cylindrical inner surface 68 are formed between edges 60 and 62. A central cylindrical chamber, or aperture, 76 is formed within implant 10, between edges 60 and 62. Chamber 76 extends between and includes open leading end 80 and an open trailing end 82 within implant 10. Upon implantation, open leading end 80 entraps projections 54 and 56 as shown in FIGS. 15 and 18 which imparts immediate fixation between vertebral bodies 12 and 14.

As shown in FIGS. 6–12, cylindrical outer surface 66 of implant 10 comprises a smooth, leading end insertion portion 70 and a bone engaging, or interlocking, trailing end, retaining portion 72. Smooth leading, insertion portion 70 extends generally from leading edge 60 rearwardly along cylindrical outer surface 66 to an approximately midposition there along. Bone engaging, or interlocking, trailing portion 72 begins where smooth, insertion portion 70 terminates and extends rearwardly to trailing edge 62. According to one construction, smooth leading, insertion portion 70 comprises generally in the range of 10%–90% of the axial length of cylindrical outer surface 66. According to another construction, smooth leading, insertion portion 70 extends from 30%–60% of the axial length of cylindrical outer surface 66. According to yet another construction, smooth leading, insertion portion 70 extends along the axial distance of cylindrical surface 66 to a length sufficient to provide for a sufficient amount of retaining devices, such as threads 74, to retain implant 10 upon insertion between bone beds of adjacent vertebral bodies.

In assembly, smooth insertion portion 70 facilitates self-alignment when inserting insertion portion 70 into aperture 18 (see FIGS. 14 and 15). Retaining portion 72 is then driven in rotation into aperture 18 such that self-tapping threads 74 instantly fix implant 10 within aperture 18 so as to prevent ejection therefrom.

Also shown in FIGS. 6–12, a plurality of fenestrations 78 are provided spaced apart and extending through the tubular wall of implant 10. Such fenestrations 78 serve to facilitate bony ingrowth and through growth, and generally staged fusion as discussed in U.S. Pat. No. 5,709,683 incorporated herein by reference. Fenestrations 78 also interrupt thread 74 so as provide cutting surfaces that render thread 74 self-tapping.

Such bony ingrowth and through-growth occur following insertion of implant 10 within bone beds defined by inner surfaces 160 and 164 and outer surfaces 162 and 166 as shown in FIGS. 14 and 15. More particularly, remodeled bony ingrowth and through-growth are shown and described below in FIGS. 20 and 21. Fenestrations 78 extend substantially throughout the circumferential wall of tubular implant 10, particularly as shown in FIG. 6 and 7. Such fenestrations 78 offer avenues of ingrowth of bone between vertebrae, which is stimulated by bone chips 134 (see FIG. 19) that are placed within a central chamber comprising cylindrical aperture 76 (see FIG. 6). In this manner, fenestrations 78 serve to facilitate earlier and more thorough ingrowth of bone within implant 10. Furthermore, fenestrations 78 enhance overall through growth of bone through implant 10.

According to FIG. 11, cylindrical outer surface 66 (see FIG. 6) of implant 10 is shown in an unrolled plan view to better depict layout of fenestrations 78 and thread 74. A leading end tapered portion 64 is also shown extending along and immediately adjacent to leading edge 60. FIG. 12 further illustrates surface 66.

An additional feature of Applicant's invention is provided by tapered portion 64. Leading edge 60 is inserted into an appropriately sized aperture 18 (see FIG. 14), and insertion pressure is applied sufficient to generate distraction between adjacent vertebrae as leading tapered portion 64 is inserted therein. Hence, vertebrae 12 and 14 are slightly distracted during insertion of implant 10 therebetween.

Figure 13:
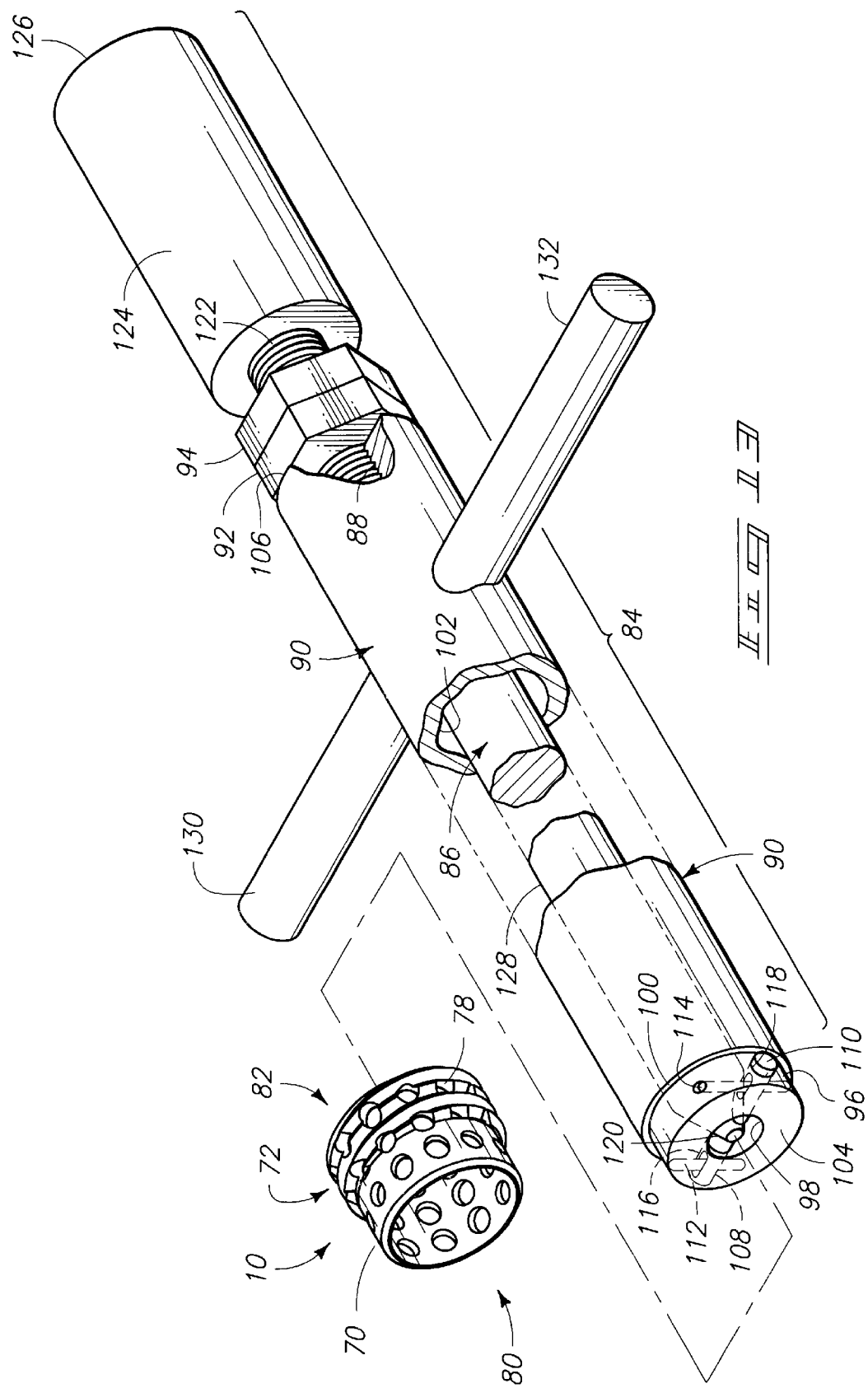
FIG. 13 a perspective view illustrating an implant insertion tool usable for inserting and threading the implant of FIGS. 12–16 within the prepared bone beds of FIG. 5.

FIG. 13 illustrates an insertion tool or instrument 84 configured for loading implant 10 into prepared bone beds formed by kerf 1042 and bore 38 (see FIG. 6). More particularly, bone beds are provided by a pair of inner surfaces 160, 164 and a pair of outer surfaces 162, 166 formed at least in part by kerf 1042 as viewed in FIGS. 14 and 15.

Insertion tool 84 is formed from a driver 86 and a guide 90. Guide 90 forms a threaded bore 88 in which driver 86 is received in adjustable, threaded engagement via threaded portion 122 of driver 86. An adjustment nut 92 cooperates with a lock nut 94 to enable securement of driver 86 within guide 90 at a desired, threaded axial location.

Once driver 86 has been threaded sufficiently into guide 90 to cause pins 108 and 110 to be moved outwardly via contact with end 120, nut 92 is tightened into engagement against trailing end 106. Subsequently, lock nut 94 is tightened into engagement against nut 92.

A recessed mounting surface 96 is formed adjacent a leading end 104 of guide 90. Surface 96 is sized to slidably fit securely within open trailing end 82 (see FIGS. 7 and 10) of implant 10. Once positioned over surface 96 and against a receiving shelf 100, implant 10 is locked onto guide 90 by outwardly biasing a pair of retaining pins 108 and 110 within tool fenestrations 78. Preferably, pins 108 and 110 are sized to fit within fenestrations 78. Hence, pins 108 and 110 are sized to prevent misaligned mounting of implant 10 onto insertion tool 84.

More particularly, driver 86 forms a driver pin 128 that extends within an enlarged bore 102 formed within guide 90. Bore 102 decreases in size immediately adjacent leading end 104 so as to form a reduced diameter bore 98. Bore 98 enables clearance of a beveled frustoconical end 120 of driver pin 128 during threaded adjustment between driver 86 and guide 90. Frustoconical end 120 mates in sliding engagement with a radially inwardly extending end of each pin 108 and 110. Such inward end of each pin 108 and 110 forms a complementary beveled end that mates for sliding engagement with end 120 as driver 86 is adjustably positioned within guide 90.

Pins 108 and 110 are retained for radially extending inward/outward movement within associated guide holes 116 and 118, respectively. More particularly, each pin 108 and 110 is retained within holes 116 and 118 via a press-fit rolled pin 112 and 114, respectively. Each rolled pin 112 and 114 passes through an elongated slot formed through each associated pin 112 and 114. In this manner, each pin 112 and 114 is allowed to slide within guide hole 116 and 118, respectively, but is prevented from becoming completely dislodged.

In order to facilitate aligned axial insertion of implant 10, driver 86 has an enlarged driver handle 124 that terminates to form a driver end 126. To insert subsequent fixation of implant 10 within bone beds, driver 86 has a pair of driver handles 130 and 132 which facilitate rotation of implant 10 to drive threads 78 into interlocking, self-tapping and fixed engagement within such bone beds so as to secure aligned implant 10 therebetween.

Driver end 126 is shaped to facilitate impact with a hammer during insertion of an implant 10 between bone bodies, although the need for such impact is significantly reduced or eliminated due to the self-aligning insertion features provided by implant 10. Optionally, implant 10 can first be inserted between bone beds by hand, after which driver 86 is secured to a rear edge of implant 10 to rotatably drive implant 10 and engage thread 78 therein. Accordingly, smooth insertion portion 70 facilitates either hand or tool placement of implant 10 in a self-aligning manner. For the case where driver 86 is used to insert smooth insertion portion 70, driver 86 further ensures such alignment during placement. Subsequently, driver 86 is used to drive thread 78 of interlocking trailing portion 72 into engagement therebetween.

Furthermore, pins 108 and 110 cooperate with recessed mounting surface 96 and shelf 100 to rigidly and securely retain implant 10 on tool 84, even where considerable lateral loading might occur. Such lateral loading might occur, for example, as a result of wiggling implant 10 and tool 84 while attempting to drive implant 10 within and between a pair of prepared vertebrae. Upon insertion, implant 10 traps adjacent vertebrae for immediate fixation, within open leading end 80.

Once implant 10 has been inserted between bone bodies, nuts 92 and 94 are loosened, after which driver 86 is loosened or unthreaded relative to guide 90 which enables pins 108 and 110 to retract. Preferably, the outermost ends of pins 108 and 110 are chamfered to facilitate removal of implant 10 from tool 84. Optionally, frustoconical end 120 can be magnetized to impart retraction of pins 108 and 110 as drive pin 128 is retracted within guide 90.

Figure 20:
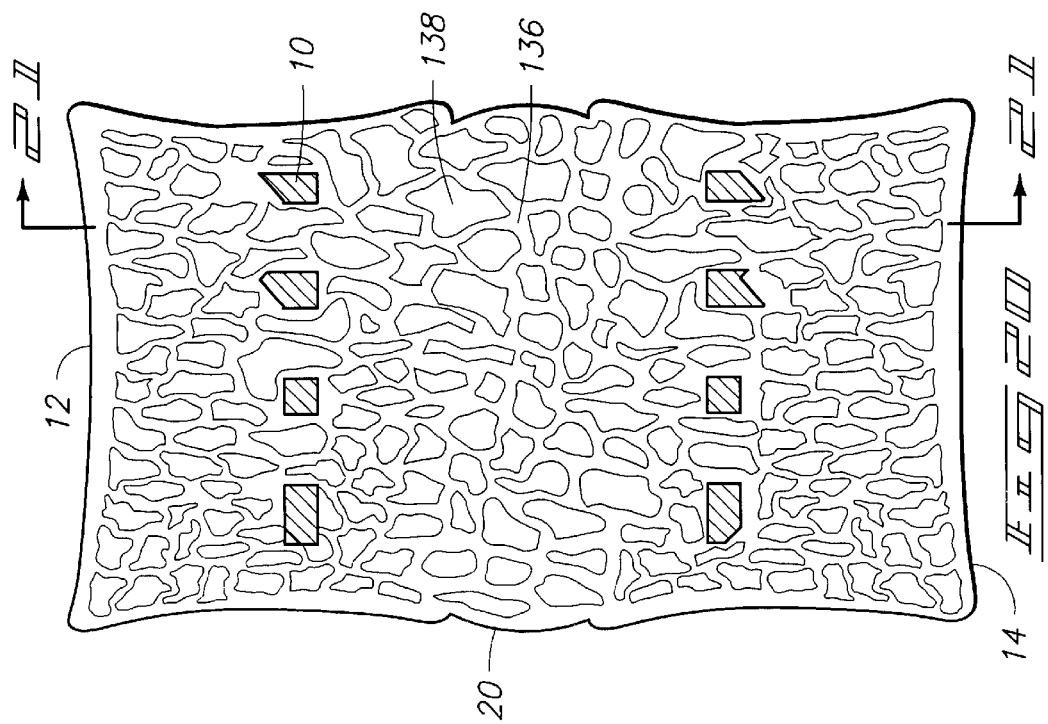
FIG. 20 is a healed time simplified sagittal view of the implant of FIG. 19 received within the prepared bone beds of adjacent vertebrae and illustrating the vertebra following bone remodeling and reorganization and showing arthrodesis.
Figure 19:
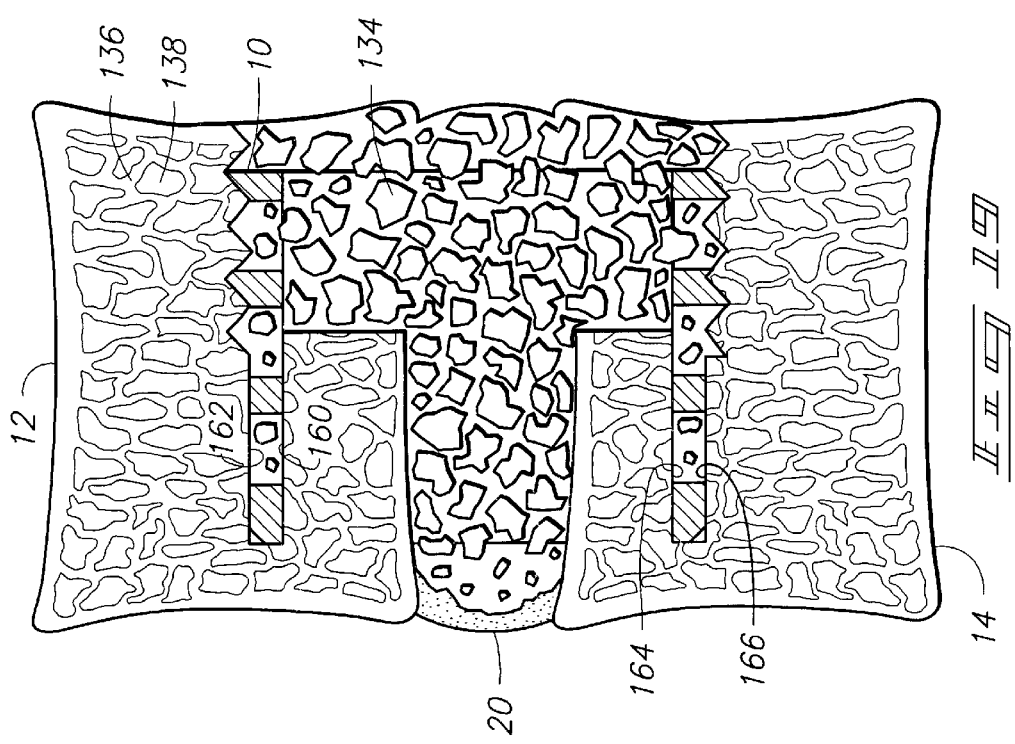
FIG. 19 is a surgical time simplified sagittal view of the implant of FIG. 18 received within the prepared bone beds of adjacent vertebrae and containing bone fragments immediately following implantation.

FIGS. 19 and 20 illustrate prepared vertebrae 12 and 14 prior to insertion of an implant and after insertion of an implant of Applicant's invention, respectively, but with the implant omitted for clarity. FIG. 21 corresponds with FIG. 20, but shows the details of implant 10 inserted in self-aligned and self-fixated, interlocking relation with vertebrae 12 and 14.

As shown in FIG. 15, a pair of vertebrae 12 and 14 are retained together with a partially removed intervertebral disc 20. An aperture 18 is formed partially as a kerf 1042 (see FIG. 14), and generates bone beds in the form of inner surfaces 160, 164 and outer surfaces 162, 166. A pair of intact bone projections 54 and 56 are formed as a result, extending from vertebrae 12 and 14, respectively. Such bone projections 54 and 56 are entrapped within the open leading end 96 of implant 10 (see FIG. 12) immediately upon insertion. Hence, instant fixation is provided upon implant of such device. Furthermore, instant distraction is also generated as a result of the tapered portion 64 of implant 10 (see FIG. 9).

FIG. 16 shows implant 10 prior to insertion between vertebrae 12 and 14. Bone projections 54 and 56 are clearly shown prior to being entrapped within implant 10 upon insertion. As shown in FIG. 16, smooth insertion portion 70 is smoothly inserted into aperture 18 either by hand or using driver 84 (of FIG. 13) until interlocking trailing portion 72 reaches a leading end of aperture 18. It is understood that smooth insertion portion 70 is sized with a diameter similar to an inner diameter of aperture 18 (as defined by bore 38) such that smooth, slidable and axially aligned engagement occurs between smooth insertion portion 70 and bore 38. The provision of smooth insertion portion 70 contributes to significantly overcoming a prior art problem wherein a typical threaded implant is susceptible of being misaligned during such initial insertion stage because it is very difficult to align implant 10 with bore 38 of aperture 18. Because vertebral bodies 12 and 14 are relatively soft in relation to the metal used to construct implant 10, the likelihood of misthreading and misalignment using prior art techniques is made even more problematic. Accordingly, it is understood that a smooth insertion portion 70 requires a sufficiently long axial portion to impart alignment of implant 10 within bore 38. According to the embodiment depicted in FIG. 16, smooth insertion portion 70 comprises approximately 50% of the axial length of implant 10 such that interlocking trailing portion 72 is sized in substantially the same length as smooth insertion portion 70. However, it is understood that smooth insertion portion 70 can occupy either a smaller percentage of the outer surface of implant 10 or a greater percentage, as long as sufficient retention is provided by interlocking trailing portion 72 so as to retain implant 10 within aperture 18.

FIG. 17 illustrates implant 10 after smooth insertion portion 72 has been received within bore 38, but prior to engaging interlocking a trailing portion 72 therein. Additionally, FIG. 17 illustrates a substantial portion of disc 20 prior to insertion of implant 10 so as to facilitate arthrodesis as discussed below.

It is understood that the placement depicted in FIG. 17 comprises an axial insertion of implant 10 within bore 38. Subsequent to such placement, a rotational insertion is imparted as described below with reference to FIG. 18 to engage interlocking trailing portion 72 and self-tapping thread 74 therein.

In FIG. 18, implant 10 is shown completely driven into position between vertebral bodies 12 and 14 so as to entrap bone projections 54 and 56, and instantly fix adjacent vertebrae 12 and 14 together. Implant 10 is illustrated mounted onto guide 90 of insertion tool 84 (of FIG. 13). Such insertion tool has been used to rotatably self-tap helical thread 74 into vertebrae 12 and 14 so as to securely retain implant 10 therein.

It is understood that the step of threadingly engaging implant 10 between vertebrae 12 and 14 significantly reduces any risk posed by fully tapping in an alternative construction implant that has a smooth, cylindrical outer surface. Such tapping might result in injury to the adjacent spinal cord, or further injury or damage to vertebrae 12 and 14, particularly in light of the construction of bone projections 54 and 56 according to the surgical procedure provided herein. It has been found that the provision of self-tapping threads on the interlocking trailing portion of implant 10 provides for more precise final placement of implant 10 within the prepared bone beds of vertebrae 12 and 14 such that any risk that bone projections 54 and 56 might break is significantly reduced or eliminated. Upon rotatable engagement of thread 72, the insertion tool is removed by retracting the pins, such as pin 110, and leaving implant 10 between vertebrae 12 and 14. After removal and retraction of insertion tool 84, bone chips, or morsels, 134 are then packed inside and around the end of implant 10, as shown in FIG. 19.

According to FIG. 19, bone chips 134, recovered when preparing vertebrae 12 and 14, facilitate earlier bone ingrowth and through growth and eliminate the need to recover bone graft from a second surgical site. For example, debris 58 (of FIG. 5) can be used to provide bone chips 134. Similarly, fenestrations, as well as the open leading and trailing ends, of implant 10 further facilitate such ingrowth and through growth.

FIG. 20 illustrates staged stabilization and fusion via Wolff's law, wherein bone remodeling and reorganization has further fixed and fused such adjacent vertebrae 12 and 14. The trabeculae relocate through fenestrations to form a mature strengthening of the trabeculae. Additional reorganization is provided by preparing bone beds that recess implant 10 within vertebrae, and by providing bone graft material thereabout at the time of implantation. Accordingly, additional bone reorganization is facilitated outside of implant 10.

More particularly, FIG. 20 is a sagittal section and diagrammatic view through implant 10 and vertebrae 12 and 14, illustrating reorganization of fused bone material through implant 10. Histologic bone cell geometry is shown in greater detail, corresponding in time with complete bone remodeling. Lacunae and canals or voids 138 are formed between the bone 136.

FIG. 21 is a coronal and diagrammatic view taken perpendicular to the view of FIG. 20 along line 21—21. In such view, bone cells have remodeled to form a definite elongated configuration extending between vertebrae 12 and 14. Such remodeled bone through growth can be seen between fenestrations on some sides of a patient, occurring from cephalad to caudad, as well as between fenestrations along a diagonal configuration of the patient, from cephalad to caudad.

FIGS. 21–24 illustrate three alternative embodiment self-aligning and self-fixating implants 1010, 2010, and 3010, respectively. More particularly, bone joining implant 1010 of FIG. 22 is shown in perspective view, and is constructed in a manner similar to implant 10 of FIGS. 6–12. Implant 1010 includes a smooth insertion portion 1070 and an interlocking trailing portion 1072. Interlocking trailing portion 1072 includes at least one helical thread 1074. Additionally, insertion portion 1070 and trailing portion 1072 each include a plurality of fenestrations 78. However, implant 1010 also includes a slightly smaller sized cylindrical aperture 1076 encircled by a rib, or bulkhead, 77. It is understood that another rib is provided centrally of implant 1010, as well as at a rearmost edge of implant 1010. One layer of such ribs is presently understood in the art, and is described in U.S. Pat. No. 5,489,308 to Kuslich, et al., herein incorporated by reference. However, the provision of rib 77 eliminates the possibility of entrapping bone projections of adjacent vertebrae such that instant fixation is not achieved when utilizing the implant of FIG. 22. However, smooth insertion portion 1070 provides for self-alignment according to the present novel aspects, and interlocking trailing portion 1072 ensures fixation of implant 1010 between bone beds upon implantation.

FIG. 23 illustrates a second alternative embodiment having a generally square, or rectangular, cross-section. Such cross-section extends with a substantially uniform outer peripheral dimension along the entire axial length of implant 2010. Implant 2010 includes a smooth insertion portion 2070 and an interlocking trailing portion 2072. Furthermore, smooth insertion portion 2070 includes a tapered 2064 along a leading end. A rectangular aperture 2076 enables instant fixation of rectangular bone projections which are prepared similar to bone projections 54 and 56 (of FIG. 17), but require a different set of tools in order to carve out such a rectangular configuration within the vertebrae. According to one placement, a single implant 2010 is used to instantly fix bone projections on adjacent vertebrae. According to another implementation, a pair of side-by-side implants 2010 are used to instantly fix two pairs of bone projections between adjacent vertebrae.

As shown in FIG. 23, interlocking trailing portion 2072 comprises a plurality of retaining tabs 1174 provided on all four faces of the outer surface of interlocking trailing portion 2072. Retaining tabs 1174 extend above such surface and are configured to engage within one of the bone beds formed within adjacent vertebral bodies that are being joined together. Such retaining tabs, or fingers, comprise a ramped front face and a sharp rear edge that serves to facilitate insertion of implant 2010 between prepared bone beds, while preventing dislodgement therefrom. More particularly, the sharp rear edges of retaining tabs 1174 serve to engage with such bone beds, preventing inadvertent dislodgement of implant 2010 from between a pair of prepared bone beds.

FIG. 24 illustrates a third alternative embodiment comprising implant 3010. Implant 3010 includes a smooth insertion portion 3070 and an interlocking trailing portion 3072. Implant 3010 is similar to implant 10 of FIGS. 6–12, with the exception of interlocking trailing portion 3072 comprising a plurality of retaining tabs 1274, similar to retaining tabs 1174 (of FIG. 3). Such tabs 1274 are also configured to engage with each bone bed formed in adjacent vertebral bodies which are being joined together by implant 3010. Implant 3010 also includes a cylindrical aperture 3076 that extends completely therethrough, and which facilitates entrapment of bone projections similar to bone projections 54 and 56 (of FIG. 16).

Each of the alternative embodiments depicted in FIGS. 22–24 are provided with the self-aligning improvement features of Applicant's present effort by provision of smooth insertion portion 1070, 2070, and 3070, respectively. Additionally, each implant 1010, 2010, and 3010 is provided with self-fixation (or retention) features via interlocking trailing portion 1072, 2072, and 3072, respectively.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. An intervertebral implant, comprising:
   a tubular body having an axially extending outer surface including a smooth leading insertion portion configured to self-align the tubular body and a bone-engaging trailing portion, the outer surface including opposed portions adapted for placement toward and adjacent each of a pair of adjacent vertebral bodies.

2. The intervertebral implant of claim 1 wherein the tubular body comprises a hollow cylinder.

3. The intervertebral implant of claim 2 wherein the trailing portion comprises at least one thread segment.

4. The intervertebral implant of claim 3 wherein the thread segment comprises a self-tapping thread.

5. The intervertebral implant of claim 2 wherein the tubular body defines a substantially constant diameter inner bore extending from an open leading end to an open trailing end.

6. The intervertebral implant of claim 5 wherein a plurality of fenestrations are provided through the tubular body extending from an outer surface adjacent living bone to an inner surface adjacent living bone to facilitate living bone growing between the inner surface and the outer surface.

7. The intervertebral implant of claim 6 wherein a tapered portion is provided along a leading end of the leading insertion portion.

8. An intervertebral wedge, comprising:
   a perforated fusion body having an outer surface including an insertion portion with an axially extending uniform cross-sectional dimension adjacent a leading end and a bone fixating trailing portion adjacent a trailing end, the insertion portion configured to self-align the fusion body between a pair of adjacent vertebra and including an open leading end defining a bore therein sized sufficiently to receive a pair of adjacent bone projections from the vertebrae to facilitate arthrodesis therebetween.

9. The intervertebral wedge of claim 8 wherein the fusion body comprises a tubular cylinder including a plurality of fenestrations extending from the outer surface to an inner surface.

10. The intervertebral wedge of claim 8 wherein the insertion portion comprises a smooth insertion portion including a substantially smooth, cylindrical leading end portion having a plurality of fenestrations extending from the outer surface to an inner surface.

11. The intervertebral wedge of claim 8 wherein the bone fixating trailing portion comprises a cylindrical threaded end portion.

12. The intervertebral wedge of claim 8 wherein the bone fixating trailing portion comprises a self-tapping thread.

13. The intervertebral wedge of claim 8 further comprising a tapered portion provided about a leading end of the insertion portion and configured to impart distraction between a pair of vertebrae upon insertion of the fusion device between a pair of bone bodies of adjacent vertebrae.

14. A vertebral fusion implant, comprising,
   an elongate, axially extending fusion body including an outer surface having an insertion portion and a threaded trailing portion, the outer surface including opposed portions adapted for placement toward each of a pair of adjacent vertebral bodies, the insertion portion having an axially extending uniform cross-section, and the threaded trailing portion provided at a trailing end of the fusion body;
   wherein the insertion portion is configured to self-align the fusion body between bone beds of adjacent vertebrae during implantation, and the threaded trailing portion is configured to self-fixate the fusion body between the bone beds.

15. The vertebral fusion implant of claim 14 wherein the fusion body comprises an elongate cylinder.

16. The vertebral fusion implant of claim 15 further comprising a plurality of fenestrations provided in the elongate cylinder extending from an outer surface to an inner surface and operative to encourage arthrodesis.

17. A spinal arthrodesis device, comprising:
   an axially extending tubular body having a smooth, leading end insertion portion, a bone-engaging trailing end portion, and a surface, the surface including opposed portions adapted for placement toward and adjacent each of a pair of adjacent vertebral bodies and the insertion portion configured to self-align the body between the pair of adjacent vertebral bodies.

18. The spinal arthrodesis device of claim 17 wherein the surface comprises an outer surface of the tubular body including an upper opposed portion adapted to contact and invade a first vertebral body and a lower opposed portion adapted to contact and invade a second, adjacent vertebral body.

19. The spinal arthrodesis device of claim 17 further comprising a bore extending from a leading end of the tubular body and invading the body, the bore of sufficient size to receive living bone projections from each of a pair of adjacent vertebral bodies.

20. The spinal arthrodesis device of claim 19 wherein the surface comprises an inner surface provided by the bore, and wherein the opposed portions comprise opposed arcuate portions of the bore adapted for placement toward and adjacent bone projections from each of a pair of adjacent vertebral bodies.

21. The spinal arthrodesis device of claim 20 wherein the bore is configured to telescopically receive the adjacent bone projections within the tubular body.

22. An intervertebral implant, comprising:
   a tubular body having a smooth leading end insertion portion configured to align the implant and a trailing end bone-engaging portion, the insertion portion including at least one wall providing an axially extending bore within the insertion portion and providing an open leading end and a first wall portion provided for insertion within a kerf of a first vertebral body and a second, opposed wall portion provided for insertion within a kerf of a second vertebral body.

23. The intervertebral implant of claim 22 wherein the first wall portion is configured to invade a first vertebral body and the second wall portion is configured to invade a second vertebral body by inserting the implant axially along an inter-disc space between the first and second vertebral bodies, and wherein respective bone projections of the vertebral bodies are telescopically received within the bore to facilitate arthrodesis between the adjacent vertebral bodies.

24. The intervertebral implant of claim 22 wherein the tubular body comprises a cylindrical body and the trailing end bone-engaging portion comprises at least one thread segment extending from the cylindrical body.

25. The intervertebral implant of claim 22 wherein the tubular leading end insertion portion comprises a cylindrical tube, the first wall comprises an arcuate portion of the cylindrical tube, and the second wall comprises an opposed, arcuate portion of the cylindrical tube.

26. The intervertebral implant of claim 25 wherein the bore extends completely through the body from an open leading end to an open trailing end, and the body comprises a cylindrical tube having a bore sized sufficiently to receive each of a pair of bone projections from respective adjacent vertebral bodies.

27. A spinal arthrodesis device, comprising:
a tubular body configured for insertion along an axis substantially parallel with an inter-disc gap between adjacent vertebral bodies, the tubular body having a smooth leading end portion configured to align the tubular body during insertion, a bone-engaging trailing end portion, a length sized to fit between the adjacent vertebral bodies, and a cross-sectional dimension sufficient to provide a bore sized to receive living bone projections from each of the adjacent vertebral bodies.

28. The spinal arthrodesis device of claim 27 wherein the tubular body has an open leading end including at least one wall configured to be received within a kerf within each of the adjacent vertebral bodies.

29. The spinal arthrodesis device of claim 28 wherein the tubular body comprises a hollow cylinder having an open leading end, defining a bore sized sufficiently to telescopically receive a bone projection from each respective vertebral body.

30. An intervertebral implant, comprising:
an elongate body having a smooth leading end portion configured to self-align the elongate body between adjacent vertebral bodies, a bone-engaging trailing end portion, and opposed lateral portions each adapted for placement toward and at least partly within the respective, adjacent vertebral bodies.

31. The intervertebral implant of claim 30 wherein the elongate body comprises a tubular body having a central axis configured for insertion along an inter-disc space between the adjacent vertebral bodies.

32. The intervertebral implant of claim 31 wherein the elongate body has an open leading end sized sufficiently to receive a bone projection from each of an adjacent pair of bone bodies.

33. An intervertebral implant, comprising:
an elongate body having a leading end configured to self-align the body between adjacent vertebral bodies comprising a smooth outer surface and a trailing end comprising at least one surface projection, the elongate body configured for alignment and Insertion substantially along a vertebral disc space between a pair of adjacent vertebral bodies, and having an open leading end communicating with a bore configured to receive a bone projection from each of the pair of adjacent vertebral bodies.

34. The intervertebral implant of claim 33 wherein the at least one surface projection comprises a thread segment.

35. A bone arthrodizing implant, comprising:
a hollow elongate body having an open front face communicating with an inner bore and an outer surface with a smooth leading end configured to self-align along adjacent bone bodies and a bone-gripping trailing end, the elongate body configured for insertion along an interface between adjacent bone bodies, and the elongate body having a cross-sectional dimension and thickness sufficient to telescopically receive vascularized bone projections from each of the adjacent bone bodies.

36. The bone arthrodizing implant of claim 35 wherein the hollow elongate body comprises a cylindrical tube having at least one thread along the bone-gripping trailing end.

37. A bone implant, comprising:
a body having a smooth leading portion configured to align the body between adjacent bone bodies, a bone-engaging trailing portion, and opposed lateral portions each adapted for placement toward adjacent bone bodies.

38. The bone implant of claim 37 wherein the body has a central axis along which the smooth leading portion and the bone-engaging trailing portion extend for axial insertion between a pair of adjacent bone bodies.

39. The bone implant of claim 38 wherein the elongate body extends at least in part within each of the adjacent bone bodies.

40. The bone implant of claim 38 wherein the body comprises a tubular body having an open leading end communicating with an internal bore having an axially extending uniform cross-sectional dimension sized sufficiently to receive a bone projection from at least one of the adjacent bone bodies.

41. The bone implant of claim 40 wherein the bore has a dimension sized sufficiently to receive each of a pair of bone projections from respective adjacent bone bodies.

42. The bone implant of claim 38 wherein the bone-engaging trailing portion comprises a thread.

43. The bone implant of claim 38 wherein the body comprises man-made material.

* * * * *

UNITED STATES PATENT AND TRADEMARK OFFICE
CERTIFICATE OF CORRECTION

PATENT NO. : 6,447,545 B1
DATED : September 10, 2002
INVENTOR(S) : George W. Bagby It is certified that error appears in the above-identified patent and that said Letters Patent is hereby corrected as shown below:

Column 1,
Line 11, delete "of is bone bodies", and insert -- of bone bodies --.
Line 32, delete "bone growth s[ a]nd fusion", and insert -- bone growth and fusion --.
Line 38, delete "designed for joining so together", and insert -- designed for joining together --.

Column 2,
Line 12, delete "having to use bone bank", and insert -- having to use a bone bank --.

Column 5,
Line 38, delete "Fig. 12 is sectional view", and insert -- Fig. 12 is a sectional view --.

Column 7,
Lines 24-25, delete "between vertebra 12 and 14", and insert -- between vertebrae 12 and 14 --.
Line 25, delete "by disc extending", and insert -- by disc 20 extending --.
Line 36, delete "of adjacent vertebras", and insert -- of adjacent vertebrae --.
Lines 36-37, delete "adjacent vertebra 12 and 14", and insert -- adjacent vertebrae 12 and 14 --.
Line 53, delete "interlocks adjacent vertebra 12 and 14", and insert -- interlocks adjacent vertebrae 12 and 14 --.

Column 9,
Line 14, delete "by use of hand-driven tool", and insert -- by use of a hand-driven tool --.

Column 10,
Line 26, delete "as shown in Figure 6 and 7", and insert -- as shown in Figures 6 and 7 --.

Column 12,
Line 60, delete "interlocking a trailing", and insert -- interlocking trailing --.
Lines 61-62, after "portion of disc 20", insert -- further removed, or resected, --.

UNITED STATES PATENT AND TRADEMARK OFFICE
CERTIFICATE OF CORRECTION

PATENT NO. : 6,447,545 B1
DATED : September 10, 2002
INVENTOR(S) : George W. Bagby It is certified that error appears in the above-identified patent and that said Letters Patent is hereby corrected as shown below:

<u>Column 14,</u>
Line 28, delete "a tapered 2064", and insert -- a tapered portion 2064 --

<u>Column 15,</u>
Line 38, delete "of claim 6", and insert -- of claim 5 --.

<u>Column 17,</u>
Line 37, delete "of claim 28", and insert -- of claim 27 --.

Signed and Sealed this

Eleventh Day of March, 2003

JAMES E. ROGAN
*Director of the United States Patent and Trademark Office*